(12) United States Patent
Chung et al.

(10) Patent No.: US 11,213,415 B2
(45) Date of Patent: Jan. 4, 2022

(54) MEDICAL DEVICE DELIVERY SYSTEMS AND METHODS

(71) Applicant: W. L. Gore & Associates, Inc., Newark, DE (US)

(72) Inventors: Karl R. Chung, Phoenix, AZ (US); Susan J. Rudes, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 126 days.

(21) Appl. No.: 16/485,568

(22) PCT Filed: Feb. 14, 2018

(86) PCT No.: PCT/US2018/018223
§ 371 (c)(1),
(2) Date: Aug. 13, 2019

(87) PCT Pub. No.: WO2018/152234
PCT Pub. Date: Aug. 23, 2018

(65) Prior Publication Data
US 2020/0046534 A1    Feb. 13, 2020

Related U.S. Application Data

(60) Provisional application No. 62/458,951, filed on Feb. 14, 2017.

(51) Int. Cl.
*A61F 2/966* (2013.01)
*A61M 25/01* (2006.01)
*A61M 25/00* (2006.01)

(52) U.S. Cl.
CPC ......... *A61F 2/966* (2013.01); *A61M 25/0147* (2013.01); *A61M 2025/0081* (2013.01); *A61M 2025/015* (2013.01)

(58) Field of Classification Search
CPC ............... A61F 2/966; A61M 25/0147; A61M 2025/0081; A61M 2025/015
See application file for complete search history.

(56) References Cited

U.S. PATENT DOCUMENTS 6,203,550 B1    3/2001  Olson
6,733,521 B2    5/2004  Chobotov et al.
(Continued)

FOREIGN PATENT DOCUMENTS

CN    101045022 A    10/2007
CN    101176685 A    5/2008
(Continued)

OTHER PUBLICATIONS

International Preliminary Report on Patentability received for PCT Patent Application No. PCT/US2018/018223, dated Aug. 29, 2019, 9 pages.
(Continued)

*Primary Examiner* — Richard G Louis

(57) ABSTRACT

Medical device delivery systems and methods are disclosed. In various examples, the medical device delivery system (1000) includes an elongate element (1100) including an olive (1200). The olive (1200) includes an opening that exposes a lockwire (1300) extending through a lumen of the olive (1200) such that a linking element (1500) can be coupled to the portion of the lockwire (1300) exposed by the opening, wherein the linking element (1500) provides a coupling to a medical device (1400).

28 Claims, 11 Drawing Sheets

(56) References Cited

U.S. PATENT DOCUMENTS

| | | | |
|---|---|---|---|
| 6,855,159 | B1 | 2/2005 | Tanner |
| 6,911,039 | B2 | 6/2005 | Shiu |
| 6,974,471 | B2 | 12/2005 | Van Schie |
| 7,081,132 | B2 | 7/2006 | Cook |
| 7,147,661 | B2 | 12/2006 | Chobotov |
| 7,655,034 | B2 | 2/2010 | Mitchell et al. |
| 7,837,724 | B2 | 11/2010 | Keeble |
| 7,938,851 | B2 | 5/2011 | Olson |
| 7,976,575 | B2 | 7/2011 | Hartley |
| 8,167,927 | B2 | 5/2012 | Chobotov |
| 8,241,346 | B2 | 8/2012 | Chobotov |
| 8,257,431 | B2 | 9/2012 | Henderson |
| 8,262,671 | B2 | 9/2012 | Osypka |
| 8,328,861 | B2 | 12/2012 | Martin |
| 8,361,135 | B2 | 1/2013 | Dittman |
| 8,480,725 | B2 | 7/2013 | Rasmussen |
| 8,926,682 | B2 | 1/2015 | Herbowy |
| 8,968,384 | B2 | 3/2015 | Pearson |
| 8,979,919 | B2 | 3/2015 | Goddard |
| 9,060,895 | B2 | 6/2015 | Hartley |
| 9,132,025 | B2 | 9/2015 | Aristizabal |
| 9,132,216 | B2 | 9/2015 | Farnan |
| 9,254,204 | B2 | 2/2016 | Roeder |
| 9,308,349 | B2 | 4/2016 | Rezac |
| 9,358,150 | B2 | 6/2016 | Rozanberg |
| 9,498,361 | B2 | 11/2016 | Roeder |
| 9,585,743 | B2 | 3/2017 | Cartledge |
| 9,585,774 | B2 | 3/2017 | Aristizabal |
| 9,681,968 | B2 | 6/2017 | Goetz |
| 9,700,701 | B2 | 7/2017 | Benjamin |
| 9,782,284 | B2 | 10/2017 | Hartley |
| 9,937,070 | B2 | 4/2018 | Skelton |
| 2003/0233140 | A1* | 12/2003 | Hartley ............... A61F 2/95 623/1.11 |
| 2004/0073289 | A1 | 4/2004 | Hartley |
| 2007/0293929 | A1* | 12/2007 | Aoba ................. A61F 2/95 623/1.11 |
| 2008/0140178 | A1* | 6/2008 | Rasmussen ........... A61F 2/95 623/1.11 |
| 2010/0036360 | A1 | 2/2010 | Herbowy et al. |
| 2012/0239130 | A1 | 9/2012 | Hartley et al. |
| 2014/0188210 | A1 | 7/2014 | Beard |
| 2014/0277341 | A1 | 9/2014 | Havel |
| 2016/0242798 | A1 | 8/2016 | Kugler |
| 2016/0338865 | A1 | 11/2016 | Campbell et al. |
| 2017/0172724 | A1 | 6/2017 | Cartledge |
| 2017/0281382 | A1 | 10/2017 | Lostetter |

FOREIGN PATENT DOCUMENTS

| | | |
|---|---|---|
| CN | 102365064 A | 2/2012 |
| EP | 1474074 B1 | 4/2004 |
| EP | 1441668 B1 | 1/2008 |
| EP | 1915113 B1 | 3/2010 |
| EP | 1358903 B1 | 2/2011 |
| EP | 2691038 B1 | 2/2014 |
| EP | 2749251 B1 | 7/2016 |
| EP | 2956198 B1 | 11/2017 |
| JP | 2005-535364 A | 11/2005 |
| JP | 2011-518620 A | 6/2011 |
| JP | 2013-509252 A | 3/2013 |
| WO | WO-2003101518 A1 | 12/2003 |
| WO | WO-2016187401 A1 | 11/2016 |

OTHER PUBLICATIONS

International Search Report and Written Opinion from PCT/US2018/018223, dated May 11, 2018, 15 pages.

\* cited by examiner

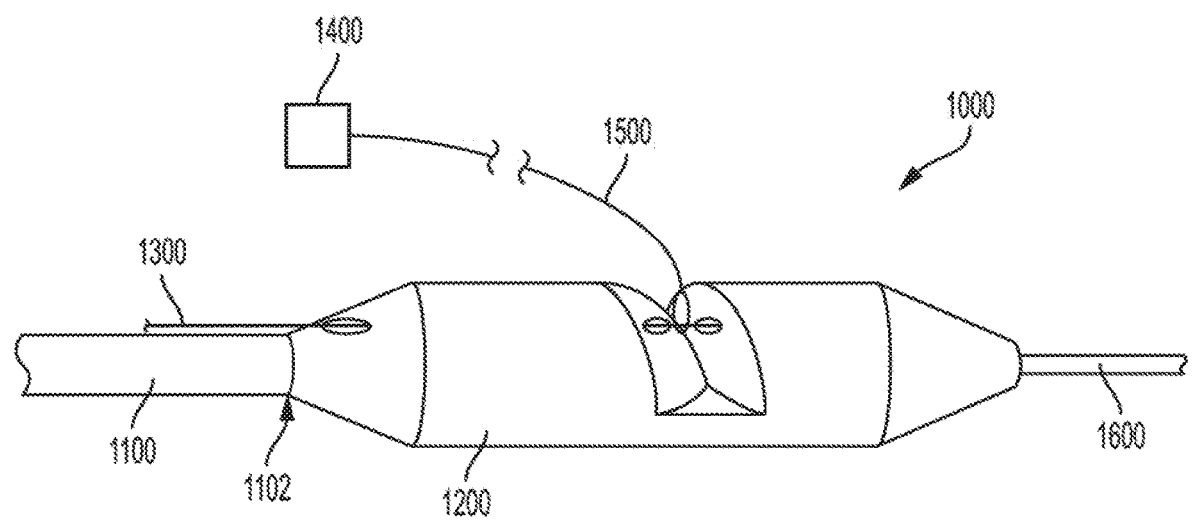
FIG. 1A
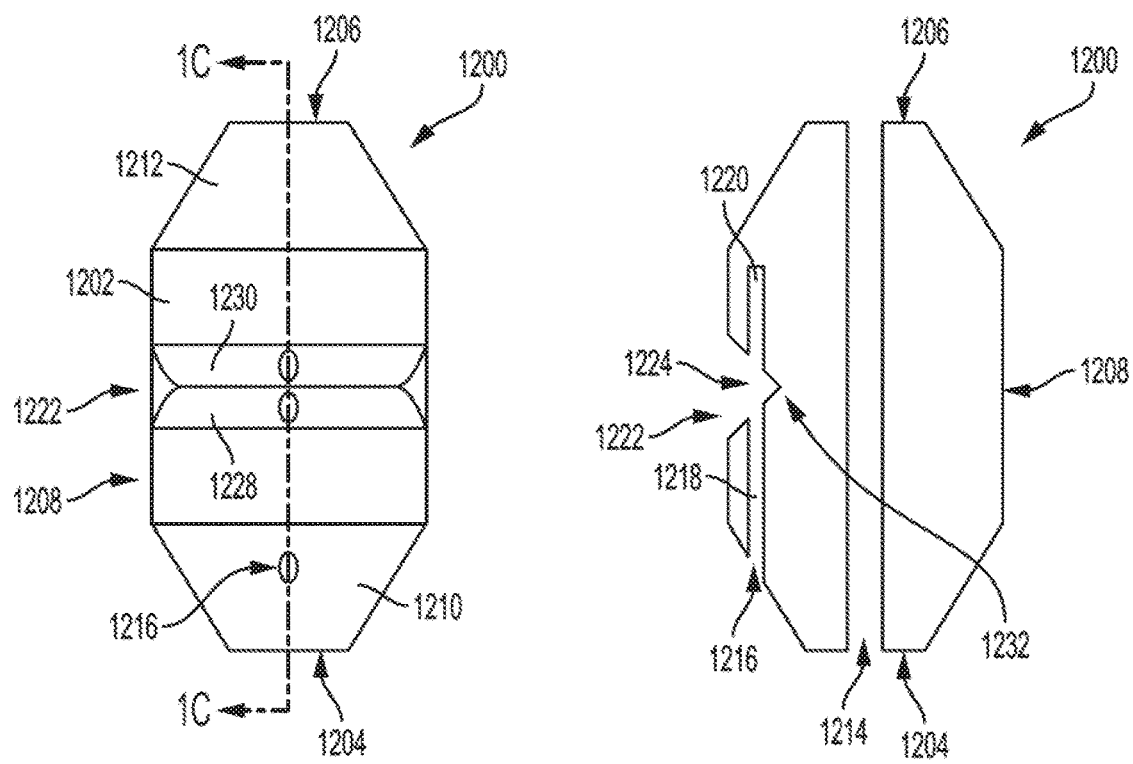
FIG. 1B
FIG. 1C

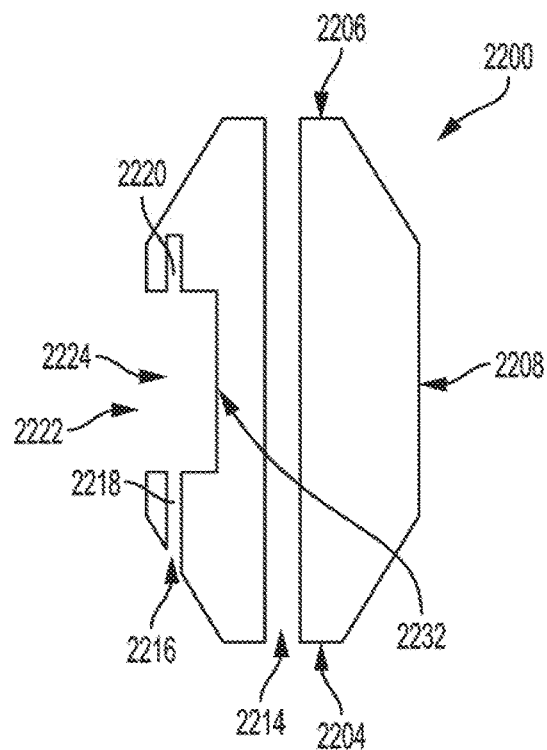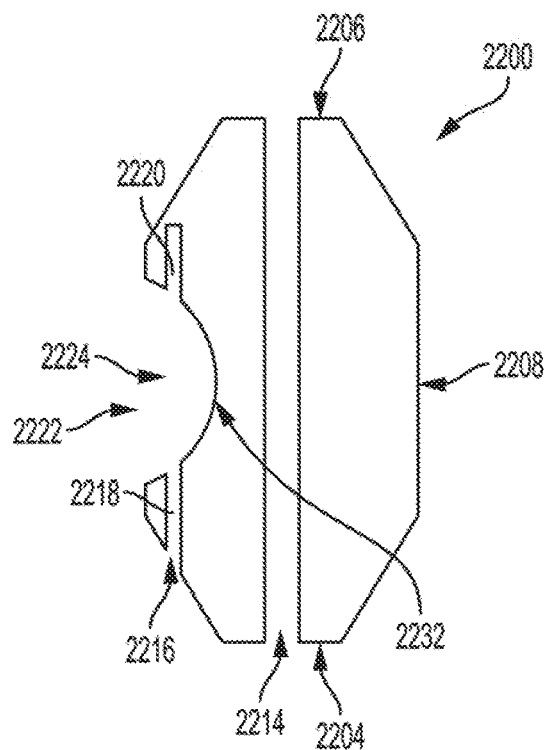
FIG. 2C
FIG. 2D
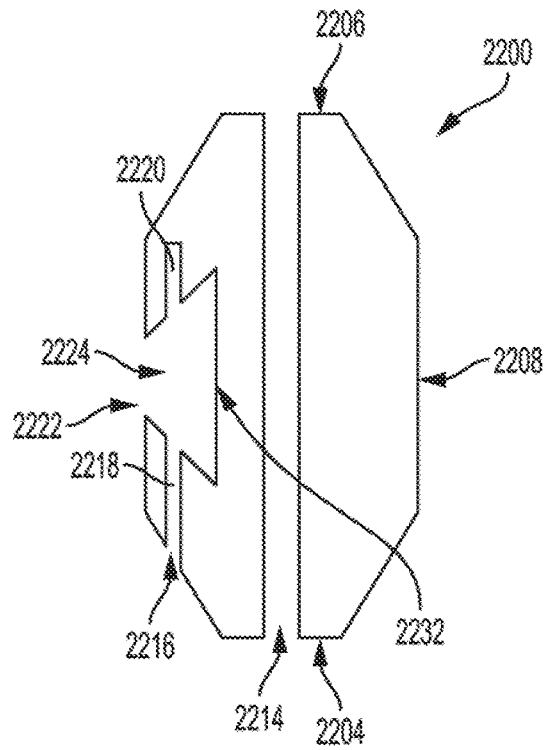
FIG. 2E

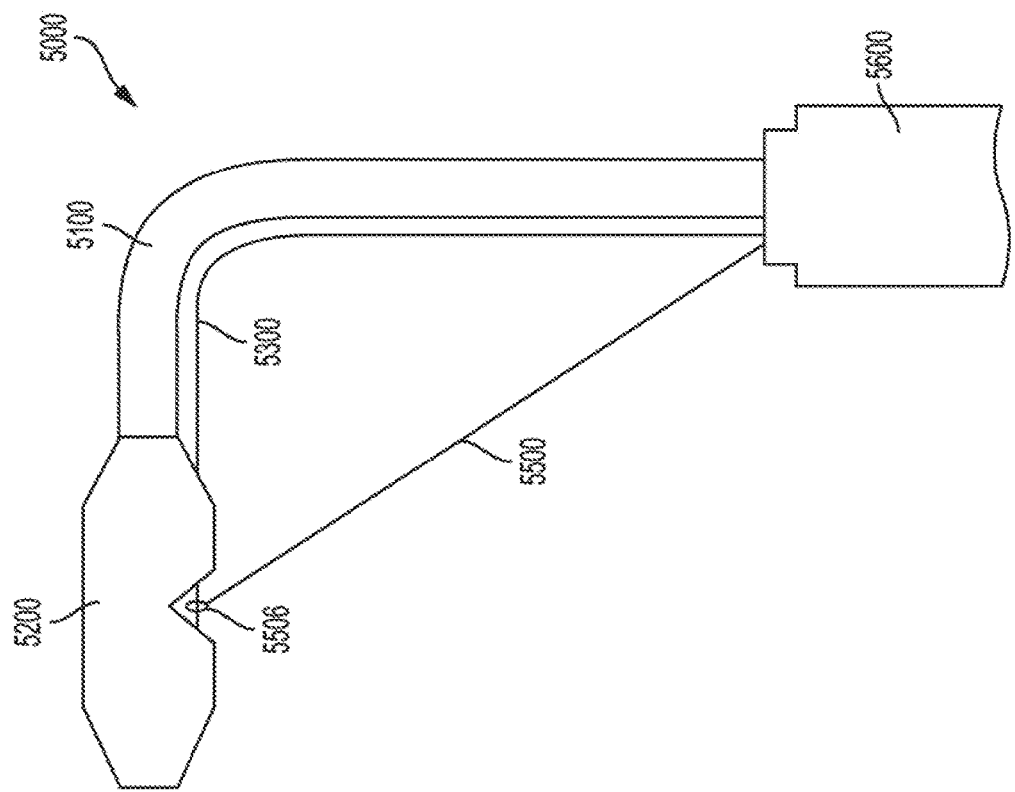
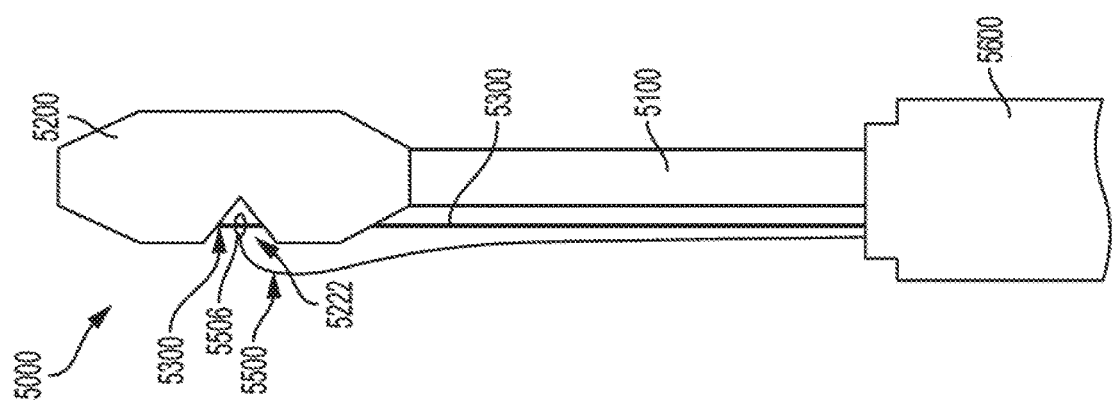

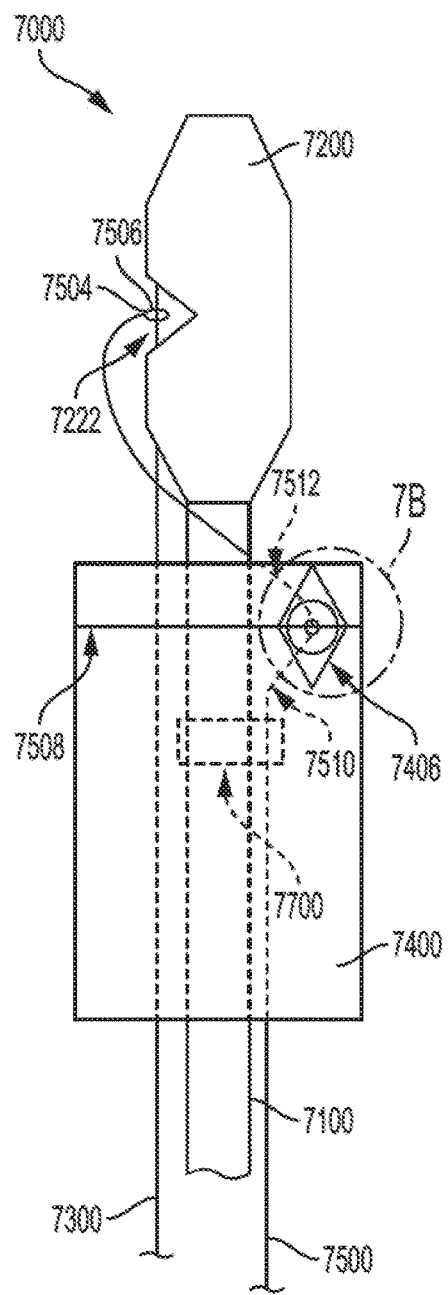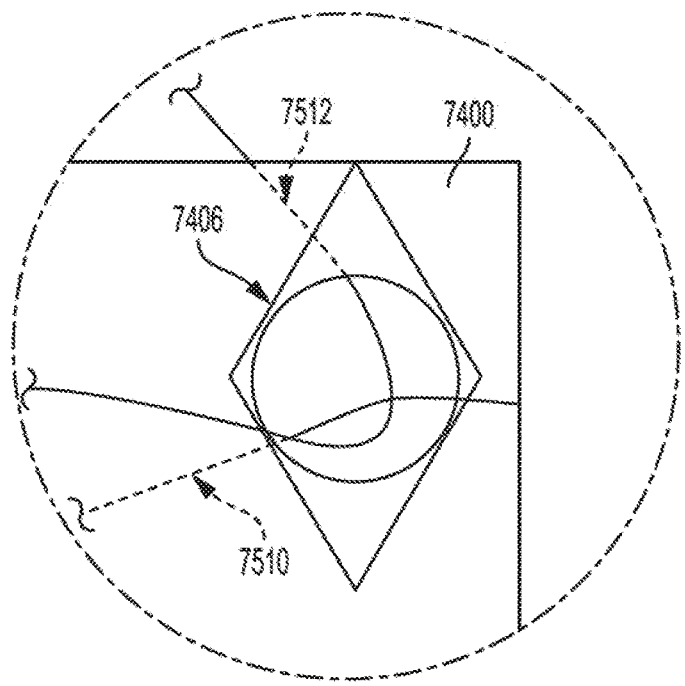
FIG. 7A
FIG. 7B

MEDICAL DEVICE DELIVERY SYSTEMS AND METHODS

CROSS-REFERENCE TO RELATED APPLICATION

[0001] This application is a U.S. 371 Application of International Application No. PCT/US2018/018223, filed Feb. 14, 2018, which claims the benefit of U.S. Provisional Application No. 62/458,951, filed Feb. 14, 2018, both of which are herein incorporated by reference in their entirety.

BACKGROUND

Endovascular procedures address a broad array of medical needs, including endovascular access, diagnosis, and/or repair through minimally invasive or relatively less invasive means than surgical approaches. Generally, these procedures require the delivery of one or more medical device to a target site or region within a patient's vasculature. One common procedure is the delivery of an expandable endoluminal device within the vasculature for the treatment of an aneurysm. Expandable endoluminal devices can be designed to expand when a restraint is removed or to be balloon-expanded from their delivery diameter, through a range of intermediary diameters, up to a maximal, pre-determined functional diameter.

Generally, the endoluminal device is constrained in a suitable introductory size (or delivery diameter) and mounted onto a delivery device such as a catheter shaft to allow insertion into the vasculature. The endoluminal devices can be difficult to navigate through vasculature. In addition, navigation through tortuous and narrow body lumens may cause the endoluminal device to migrate or otherwise translate along the delivery device upon which it is mounted.

Some conventional endovascular delivery systems utilize atraumatic tips at the distal end of the delivery device to help facilitate navigation through the vasculature. Generally, such atraumatic tips are designed to help the device navigate the vasculature without causing damage or trauma to the vasculature.

SUMMARY

According to one example, ("Example 1"), a medical device delivery system includes an elongate element, and an olive coupled to the elongate element, the olive including a body having a proximal end, a distal end, the olive including a lockwire lumen and the body having an opening formed therein, the opening being formed in the body between the proximal and distal ends such that a portion of the lockwire lumen is exposed. The medical device delivery system of Example 1, further includes a lockwire removably coupled to the olive, the lockwire extending through the lockwire lumen such that a portion of the lockwire is exposed by the opening formed in the body of the olive, and a linking element removably coupled to the portion of the lockwire extending through the lockwire lumen and exposed by the opening formed in the body of the olive.

According to another example, ("Example 2") further to Example 1, the linking element has a first end and a second end, the first end of the linking element being removably coupled to the portion of the lockwire extending through the lockwire lumen and exposed by the opening formed in the body of the olive such that the first end of the linking element is constrained against longitudinal translation along the lockwire beyond the proximal and distal ends of the olive.

According to another example, ("Example 3") further to Example 2, the linking element operates to maintain a position of a medical device along the elongate element during a delivery and deployment of the medical device to a target region within a patient's vasculature.

According to another example, ("Example 4") further to Example 3, the second end of the linking element is coupled to the medical device.

According to another example, ("Example 5") further to Example 3, the second end of the linking element is coupled to the olive such that an intermediate portion of the linking element is routed through an aperture in the medical device.

According to another example, ("Example 6") further to Example 3, the linking element includes an intermediate portion situated between the first and second ends of the linking element, the intermediate portion being coupled to the medical device and being operable to reduce a cross section of the medical device when tension is applied to the second end of the linking element.

According to another example, ("Example 7") further to Example 6, the intermediate portion of the linking element is routed about a periphery of the medical device.

According to another example, ("Example 8") further to Examples 3 to 7, the linking element is removable from the medical device.

According to another example, ("Example 9") further to any of the preceding examples, the medical device delivery system further includes a first alignment mechanism coupled to the elongate element, the linking element being routed through the first alignment mechanism.

According to another example, ("Example 10") further to Example 9, the first alignment mechanism is positioned along the elongate element such that a portion of the linking element proximal the intermediate portion is routed through the first alignment mechanism.

According to another example, ("Example 11") further to Examples 9 to 10, the medical device delivery system further includes a second alignment mechanism coupled to the elongate element, the second alignment mechanism being positioned along the elongate element such that a portion of the linking element distal the intermediate portion is routed through the second alignment mechanism.

According to another example, ("Example 12") further to Example 11, the first and second alignment mechanisms are positioned along the elongate element such that, as tension is applied to the linking element, a first longitudinally directed force exerted on medical device by the portion of the linking element extending between the first alignment mechanism and the medical device is counteracted by a second longitudinally directed force exerted on medical device by the portion of the linking element extending between the second alignment mechanism and the medical device.

According to another example, ("Example 13") further to Examples 3 to 12, a tension can be applied to the linking element to reduce a cross section of the medical device without causing translation of the medical device.

According to another example, ("Example 14") further to Examples 9 to 13, the first alignment mechanism is positioned along the elongate element such that a portion of the linking element distal the intermediate portion is routed through the first alignment mechanism.

According to another example, ("Example 15") further to any of the preceding examples, the linking element is a steering element and is operable to deflect the olive when tension is applied to the second end of the linking element.

According to another example, ("Example 16") further to any of the preceding examples, the opening formed in the body between the proximal and distal ends bisects the lockwire lumen such that the lockwire lumen includes a proximal portion and a distal portion.

According to another example, ("Example 17") further to Example 16, the proximal and distal portions of the lockwire lumen are separated by a gap, and wherein the lockwire extends across the gap such that the lockwire is received within the proximal and distal portions of the lockwire lumen.

According to another example, ("Example 18") further to any of the preceding examples, the olive further comprises a guidewire lumen, the lockwire lumen being laterally offset from the guidewire lumen.

According to another example, ("Example 19") further to any of the preceding examples, the linking element is compressible.

According to another example, ("Example 20"), a method of releasably coupling a constraining element to an olive includes, providing an olive coupled to a distal end of an elongate element, the olive including a body having a proximal end and a distal end, the olive including a lumen and the body of the olive having an opening formed therein, the opening being formed in the body of the olive between the proximal and distal ends such that a portion of the lumen is exposed and such that the opening bisects the lumen such that lumen comprises a proximal portion and a distal portion. The method further includes routing a linking element to the olive such that a portion of the linking element is positioned within the lumen of the olive, positioning a distal end of the linking element in the opening formed in the olive such that the distal end of the linking element is situated between the proximal and distal portions of the lumen, inserting a lockwire into the proximal portion of the lumen, and advancing the lockwire through the proximal portion of the lumen and into the distal portion of the lumen such that the lockwire engages the linking element and constrains a distal end of the linking element from longitudinal translation along the lockwire beyond the proximal and distal ends of the olive.

According to another example, ("Example 21"), further to Example 20, the method further includes withdrawing the lockwire from the distal portion of the lumen such that a distal end of the lockwire is positioned within the proximal portion of the lumen operates to decouple the linking element from the lockwire.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The accompanying drawings are included to provide a further understanding of inventive embodiments of the disclosure and are incorporated in and constitute a part of this specification, illustrate examples, and together with the description serve to explain inventive principles of the disclosure.

FIG. 1A is a perspective view of a medical device delivery system consistent with various aspects of the present disclosure.

FIG. 1B is a top view of the medical device delivery system of FIG. 1A consistent with various aspects of the present disclosure.

FIG. 1C is a cross sectional view of the medical device delivery system of FIGS. 1A and 1B taken along line 1C-1C consistent with various aspects of the present disclosure.

FIG. 2C is a cross sectional view of a medical device delivery system consistent with various aspects of the present disclosure.

FIG. 2D is a cross sectional view of a medical device delivery system consistent with various aspects of the present disclosure.

FIG. 2E is a cross sectional view of a medical device delivery system consistent with various aspects of the present disclosure.

FIGS. 5A and 5B illustrate a medical device delivery system consistent with various aspects of the present disclosure.

FIG. 7A illustrates a medical device delivery system consistent with various aspects of the present disclosure.

FIG. 7B is a detailed view of a portion of the medical device delivery system of FIG. 7A.

DETAILED DESCRIPTION

Figure 2A:
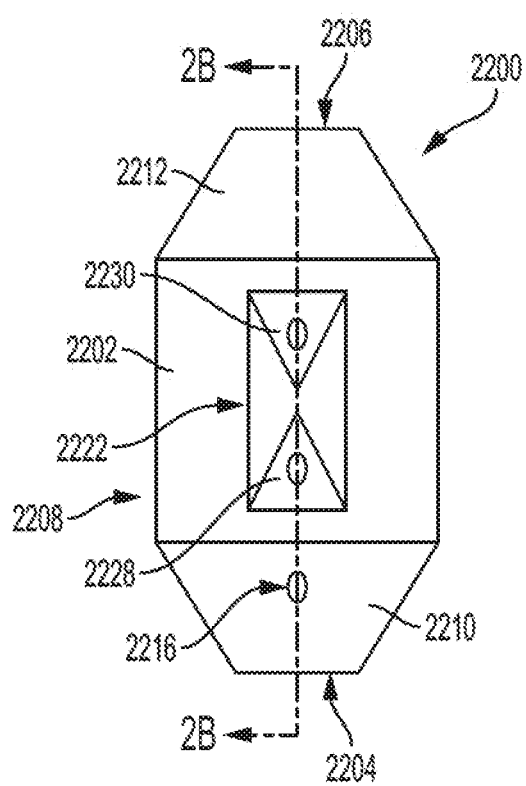
FIG. 2A is an illustration of a medical device delivery system consistent with various aspects of the present disclosure.
Figure 2B:
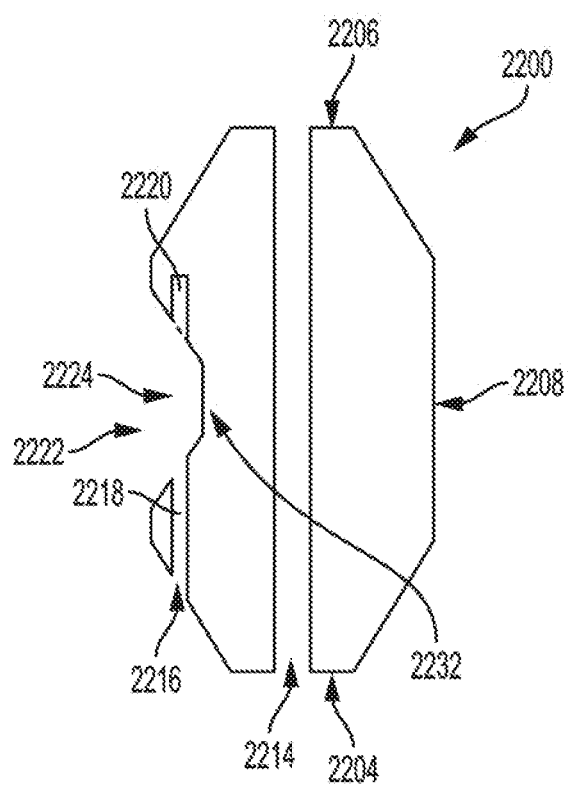
FIG. 2B is a cross sectional view of the medical device delivery system of FIG. 2A taken along line 2B-2B consistent with various aspects of the present disclosure.

Persons skilled in the art will readily appreciate that the various embodiments of the inventive concepts provided in the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. In describing various examples, the term distal is used to denote a position along an exemplary device proximate to or alternatively nearest to the treatment region within a patient's body. The term proximal is used to denote a position along the exemplary device proximate to or alternatively nearest to the user or operator of the device.

Various aspects of the present disclosure are directed toward medical device delivery devices, systems, and methods that include an atraumatic tip or olive configured for a variety of purposes or functions. A medical device delivery system according to some embodiments is illustrated in FIG. 1. The medical device delivery system 1000 includes an elongate element 1100 and an atraumatic tip or olive 1200 coupled to the elongate element 1100.

In some examples, the medical device delivery system 1000 further includes one or more lockwires 1300 that may be removably coupled to or otherwise received by the olive 1200. As discussed in greater detail below, in some examples, the lockwire operates with the olive such that one or more medical devices 1400 are removably coupleable to the olive 1200. In some such examples, one or more constraining elements (or linking elements), such as constraining fiber 1500 extend from the one or more medical devices 1400 to the one or more lockwires 1300. As discussed in greater detail below, such configurations provide for the maintaining of a position of the one or more medical devices 1400 along the elongate element 1100 during delivery to or deployment at a target site or region within the vasculature. It should be appreciated that while the examples below refer to the constraining element as a constraining fiber 1500, such reference should not be interpreted as limiting. For instance, it should be appreciated that the constraining element may be a structure that is suitable for being placed in tension, compression, or tension and compression. Likewise, those of skill in the art should appreciate that reference to the term constraining element should not be construed as being limited, but should rather be understood to include any linkage capable of structurally linking the lockwire to one or more other element of the system.

In some examples, the one or more lockwires 1300 may be additionally or alternatively removably coupleable to one or more steering lines to facilitate steering of the medical device delivery system 1000. In some examples, the medical device delivery system 1000 is operable to be delivered to a target site by being advanced over a guidewire 1600.

In various embodiments, the elongate element 1100 corresponds to a catheter shaft. In some examples, the elongate element 1100 is a flexible, elongated element having proximal and distal ends and is capable of being advanced through one or more vessels to a target site or region within the vasculature. The elongate element 1100 may be any device suitable for passage through the vasculature to a treatment region or target site. In some examples, the elongate element 1100 operates as a vehicle by which a medical device such as an endoluminal graft may be advanced to the treatment region. In some examples, the elongate element 1100 has a lumen extending through at least a portion of its length. In some examples, the lumen operates as a conduit such that the medical device delivery system 1000 can be delivered over a guide wire 1600. In some examples, the lumen additionally or alternatively operates as a working lumen that provides a passageway through which one or more medical devices (e.g., medical devices, tools, lights, and/or any other suitable therapeutic devices) may be delivered to the treatment region.

The elongate element 1100, or any portion thereof, can be comprised of any number of materials including silicone, latex, polyurethanes, polyvinyl chlorides, polyethylenes, polysiloxanes, polycarbonates, nylons, PTFE, ePTFE or other fluoropolymer, polyamides, stainless steel, nitinol, or any other biocompatible material, including combinations of the foregoing. Additionally, the elongate element 1100, or any portion thereof, can be hydrophilic or hydrophobic. In various examples, the elongate element 1100 can have any cross-sectional shape including, for example, a circular shape, an oval shape, a triangular shape, a square shape, a polygon shape, a uniform shape, or a non-uniform shape.

In various embodiments, the medical device delivery system 1000 includes an olive 1200 coupled to the elongate element 1100. In some examples, the olive is coupled at or proximate to a distal end 1102 of the elongate element 1100. The olive 1200 includes a generally tapered or frustoconically-shaped distal portion, although in some examples the distal portion does not taper. In some examples, the olive 1200 includes a generally tapered or frustoconically-shaped proximal portion, although in some examples the proximal portion does not taper.

Turning now to FIGS. 1A-1C, an exemplary olive 1200 is illustrated. Olive 1200 includes a cylindrically shaped body 1202 having a proximal end 1204, a distal end 1206, and an intermediate portion 1208 situated between the proximal and distal ends 1204 and 1206. In some examples, the body 1202 includes one or more tapered sections, such as proximal taper section 1210 and distal taper section 1212. As shown, the distal taper section 1212 decreases in outer peripheral dimension longitudinally toward the distal end 1206 of the olive 1200 while the proximal taper section 1210 decreases in outer peripheral dimension longitudinally toward the proximal end 1204 of the olive 1200. Those of skill will appreciate that the distal tapered section 1212 helps guide the atraumatic tip 1200 as it is being advanced through the vasculature and helps avoid surrounding tissue from being damaged in the event the atraumatic tip 1200 contacts the tissue as the medical device delivery system 1000 is advanced through the vasculature. The proximal tapered section 1210 helps navigation of the medical device delivery system 1000 as it is withdrawn through the medical device.

In some examples, the olive 1200 includes an inner lumen 1214 extending through at least a portion of its length. In some examples, the inner lumen 1214 extends from the proximal end 1204 to the distal end 1206 of the olive 1200 such that the lumen 1214 is exposed and accessible at both the proximal and distal ends 1204 and 1206. In some examples, the lumen 1214 is sized such that a guide wire, such as guide wire 1600 (FIG. 1A), can be passed therethrough and the medical device delivery system 1000 can be delivered to a treatment region over the guide wire. In some examples, the lumen 1214 additionally or alternatively operates as a working lumen and provides a passageway through which one or more medical devices or therapeutics may be delivered to the treatment region.

In some examples, a longitudinal axis of the inner lumen 1214 is parallel to (or substantially parallel to) a longitudinal axis of the olive 1200 (i.e., coaxial). In some examples, the longitudinal axis of the inner lumen 1214 is parallel to (or substantially parallel to) but laterally offset from a longitudinal axis of the olive 1200. In some examples, the olive 1200 is coupled to the elongate element 1100 such that the lumen 1214 of the olive 1200 is coaxial with the lumen of the elongate element 1100.

In some embodiments, the olive 1200 includes one or more lockwire lumens extending through at least a portion of its length. For example, as shown in FIGS. 1A-2E, the olive 1200 includes a lockwire lumen 1216 extending through at least a portion of its length. As shown, the lockwire lumen 1216 is formed in the proximal taper section 1210, projecting distally. However, in various examples, the lockwire lumen 1216 may be formed in the proximal end 1204. Likewise, in some examples, the lockwire lumen may be formed in a distal taper portion 1212 or the distal end 1206 and may project proximally. In some examples, the lockwire lumen 1216 may extend entirely through the olive 1200. In other examples, the lockwire lumen extends through only a portion of the length of the olive 1200.

In some examples, a longitudinal axis of the lockwire lumen 1216 is parallel to (or substantially parallel to) but laterally offset from a longitudinal axis of the inner lumen 1214 of the olive 1200. In some examples, a longitudinal axis of the lockwire lumen 1216 is nonparallel to (or not substantially parallel to) a longitudinal axis of the inner lumen 1214. That is, in some examples, a longitudinal axis of the lockwire lumen 1216 is angled relative to the longitudinal axis of the inner lumen 1214 of the olive.

As discussed below, in some examples, the lockwire lumen 1216 may include a proximal portion 1218 and a distal portion 1220 that are separated by a gap as a result of a relief being formed in the olive 1200.

The lockwire lumen 1216 is configured to receive the lockwire 1300 therein such that the lockwire may be selectively removed there-from. Such a configuration facilitates the removable coupling of the lockwire 1300 to the olive 1200. That is, the lockwire 1300 may be selectively decoupled from the olive 1200. In some examples, the lockwire lumen is formed in the olive 1200 such that its length exceeds a length of the portion of the lockwire received therein. Additionally, in some examples, a diameter of the lockwire lumen exceeds a diameter of the lockwire. For instance, in some examples, the lockwire lumen may be in the range of one (1) to three (3) thousandths of an inch larger than the lockwire. In some examples, however, the lockwire lumen may be less than one (1) thousandth of an inch larger than the lockwire, or alternatively larger than three (2) thousandths of an inch larger than the lockwire, depending on the application.

Generally, a diameter of the lockwire varies by application. For example, a lockwire utilized in association with a steering line may need to be larger in diameter than a lockwire utilized in association with a constraining fiber. However, a diameter of the lockwire need not be different for different applications. For example, as discussed below, a constraining fiber and a wire may simultaneously be coupled to a common lockwire. Exemplary diameters of lockwires are in the range of five (5) to fifteen (15) thousandths of an inch. For instance, in some examples a lockwire may be approximately nine (9) thousands of an inch in diameter. Those of skill should appreciate that the lockwire may be less than five (5) thousandths of an inch, or alternatively, larger than fifteen (15) thousandths of an inch in diameter, depending on the specific application, for example.

In some examples, the lockwire 1300 may be coupled to the olive 1200 by way of one or more threaded portions, friction or interference joints, welds, adhesives, or other suitable retention or coupling interfaces. In some such examples, the lockwire 1300 may be coupled to a first portion of the lockwire lumen 1216 while remaining uncoupled from a second portion of the lockwire lumen 1216. In some examples, by having a lockwire lumen with a diameter that exceeds the diameter of the lockwire (i.e., oversized), a force required to insert and remove the lockwire from the lockwire lumen can be minimized.

In some examples, the diameter of the lockwire lumen may vary in diameter. For example, the distal portion of the lockwire lumen may be smaller in diameter than is the proximal portion of the lockwire lumen (or vice versa). In some such examples, the lockwire lumen may progressively decrease in diameter (e.g., continuous taper). In other such examples, the lockwire lumen may decrease in diameter in steps (e.g. a discontinuous taper wherein a first portion of a length of the lockwire lumen is first diameter while a second, different portion of the length of the lockwire lumen is a second, different diameter). Likewise, in some examples, the lockwire may additionally or alternatively decrease (or alternatively increase) in diameter (progressively or in steps) along its length. Those of skill should appreciate that such examples provide for a coupling between the lockwire and the lockwire lumen where only a portion of the lockwire inserted within the lockwire lumen contacts the lockwire lumen (e.g., a distal end, or a portion that contacts a proximal end of the proximal portion of the lockwire lumen). In some examples, the lockwire may be secured to one or more control mechanisms at its proximal end.

Moreover, while the lockwire lumen 1216 is illustrated as extending through only a portion of the olive 1200, in some examples, one or more lockwire lumens may extend entirely though the olive 1200. Likewise, in some examples, the olive may include a plurality of lockwire lumens and therefore may interface with or otherwise have a plurality of lockwires coupled therewith.

In some examples, one or more lockwire exposure features, such as lockwire exposure feature 1222 may be formed in the olive 1200. In some examples, a lockwire exposure feature 1222 is formed as a relief, channel, trough, cavity, depression, or indentation in an outer surface of the olive 1200. In some examples, the lockwire exposure feature 1222 is formed by skiving or otherwise removing material from the olive 1200. While the lockwire exposure feature 1222 is illustrated as being formed in the intermediate portion 1208, it should be appreciated that the lockwire exposure feature 1222 may be formed in any portion of the olive 1200 provided that a portion of the lockwire 1300 extending therethrough is exposable by the lockwire exposure feature 1222. Generally, as discussed in greater detail below, the lockwire exposure feature 1222 facilitates a location for an attachment to the portion of the lockwire 1300 extending through the olive 1200 and exposed by the lockwire exposure feature 1222.

Those of skill in the art should appreciate that while the examples illustrated and described herein include an olive with a skived portion (e.g., a lockwire exposure feature), in some examples, the system may include an olive with a plurality of independently formed skived portions (e.g., a plurality of independent lockwire exposure features). Thus, in some examples, the lockwire lumen may be sectioned into three or more portions. In such examples, the portions of the lockwire exposed by the multiple lockwire exposure features are each coupleable to one or more constraining elements (or linking elements) consistent with the other examples illustrated and described herein. Likewise, it should be appreciated that the system may include a plurality of olives, one or more of which may include one or more skived portions.

In various embodiments, the lockwire exposure feature 1222 is generally formed in the olive 1200 such that it bisects and otherwise exposes a portion of the lockwire lumen 1216. This bisecting of the lockwire lumen 1216 operates to form the proximal and distal portions 1218 and 1220 of the lockwire lumen 1216. It should be appreciated that the lockwire exposure feature 1222 bisection of the lockwire lumen 1216 need not divide the lockwire lumen 1216 into proximal and distal portions 1218 and 1220 having equal lengths, though equal lengths are desirable in some examples.

In addition, the lockwire exposure feature 1222 is formed in the olive 1200 such that the proximal and distal portions 1218 and 1220 of the lockwire lumen 1216 are separated by a gap. As explained in greater detail below, such a gap provides that one or more medical devices and/or one or more constraining fibers can be coupled to the portion of the lockwire exposed by the lockwire exposure feature 1222 that extends across the gap form the proximal to the distal (or vice versa) of the lockwire lumen.

As shown in FIG. 1C, the proximal and distal portions 1218 and 1220 of the lockwire lumen 1216 are separated by a gap 1224. Those of skill in the art should appreciate that the relief forming the lockwire exposure feature 1222 may be of any shape or size provided that the relief exposes a portion of the lockwire lumen 1216 and does not sever or otherwise materially compromise the structural integrity of the olive 1200. As shown in FIG. 1C, the relief forming the lockwire exposure feature 1222 is a triangular relief that converges to a point as the relief progresses radially inward from an exterior surface of the olive 1200. As shown in FIGS. 1A and 1B, the triangular relief is circumferentially revolved around a portion of the olive 1200 to form the lockwire exposure feature 1222. Those of skill in the art should appreciate that different applications may require different degrees to which the relief is revolved.

For instance, the relief forming the lockwire exposure feature 1222 of FIGS. 1A-1C is revolved approximately one-hundred-eighty (180) degrees about the olive 1200. That is, as shown in FIGS. 1A-1C, the lockwire exposure feature 1222 extends around only a portion of the olive 1200. In some examples, however, the lockwire exposure feature 1222 may extend around the olive 1200 entirely. That is, in some examples, the relief forming the lockwire exposure feature 1222 of FIGS. 1A-1B may be revolved about the olive 1200 in excess of one-hundred-eighty (180) degrees, though the relief may also be revolved some amount between one-hundred-eighty (180) degrees and three-hundred-sixty (360) degrees. Likewise, in some other examples, a relief forming the lockwire exposure feature 1222 may be revolved less than one-hundred-eighty (180) degrees about the olive 1200, provided that the degree to which the relief is revolved creates a void of sufficient size and depth to provide access to the lockwire extending within the lockwire lumen 1216 such that one or more medical devices may be coupled thereto.

In some other examples, the relief may alternatively be formed as a longitudinally extending groove or channel. That is, in some examples, as an alternative to (or in combination with) being revolved, the relief is projected longitudinally (see lockwire exposure feature 2222 illustrated in FIGS. 2A-2B, for example).

While the relief forming the lockwire exposure feature is illustrated in the accompanying figures as being generally triangular, it should be appreciated that virtually all shapes are contemplated and fall with the scope of the disclosure. Thus, while some relief shapes may include geometry that generally converges as it progresses radially inward, in some examples, the geometry of the relief may not converge or may alternatively diverge as it progresses radially inward.

Additional examples of relief shapes forming alternative lockwire exposure features are illustrated in FIGS. 2C-2E. FIG. 2C illustrates a cross section of an exemplary olive having a lockwire exposure feature 2222 having a geometry that does not converge as it progresses radially inward. Such a configuration provides that the proximal and distal surfaces terminate in a base 2232 such that a gap 2224 is situated between the proximal and distal sections 2218 and 2220 of the lockwire lumen 2216. FIG. 2D illustrates a cross section of an exemplary olive having a lockwire exposure feature 2222 having a geometry that is curved or nonlinear as it progresses radially inward. Such a configuration provides that a gap 2224 is situated between the proximal and distal sections 2218 and 2220 of the lockwire lumen 2216. FIG. 2E illustrates a cross section of an exemplary olive having a lockwire exposure feature 2222 having a geometry that diverges as it progresses radially inward. Such a configuration provides that the proximal and distal surfaces terminate in a base 2232 such that a gap 2224 is situated between the proximal and distal sections 2218 and 2220 of the lockwire lumen 2216. It should be appreciated that these configurations provide lockwire exposure features having gaps 2224 of significant width without severing or otherwise materially compromising the structural integrity of the olive 2200.

Additionally, while not illustrated, in some examples, the lockwire exposure feature may be formed in the olive such that the guidewire lumen (and thus any guidewire extending therethrough) are exposed. In such configurations, the constraining element may be additionally or alternatively coupled to the portion of the guidewire extending through the guidewire lumen that is exposed by the lockwire exposure feature in a manner similar to the manner in which the constraining element is described as being coupled to the portion of the lockwire extending within the lockwire lumen and exposed by the lockwire exposure feature.

In some examples, the lockwire exposure feature is formed in the olive such that it includes a first or proximal surface and an opposing second or distal surface. In some examples, the proximal and distal surfaces converge and eventually intersect with one another, while in other examples the proximal and distal surfaces converge without intersecting with one another. Instead, the proximal and distal surfaces terminate into another surface prior to intersecting with one another. Likewise, in some examples, the proximal and distal surfaces diverge and terminate into another surface. In some examples, the proximal and distal surfaces terminate into a common surface. In some other examples, the proximal and distal surfaces terminate into different intermediate surfaces and those intermediate surfaces intersect with one another. In yet some other examples, the proximal and distal surfaces are one-and-the-same in that the relief is in the form of a semi-circle. In such examples, a transition between the proximal and distal surfaces is smooth or otherwise seamless. Thus, while some examples include the proximal and/or distal surfaces being linear, in other examples, the proximal and/or distal surfaces are nonlinear.

As discussed above, in various embodiments, the relief forming the lockwire exposure feature 1222 is formed in the olive 1200 such that a void of sufficient size and depth provides access to the lockwire lumen 1216 and the lockwire extending within the lockwire lumen 1216. Thus, the lockwire exposure feature 1222 is generally formed to have a depth that extends more radially inward than (or at least as radially inward as) the lockwire lumen 1216. Such a configuration provides that the lockwire lumen 1216 is exposed by the lockwire exposure feature 1222. For example, as shown in FIG. 1C, the relief is formed in the olive 1200 such that the lockwire lumen 1216 is positioned more radially outward than is a base 1232 of the lockwire exposure feature 1222. Such a configuration provides that a gap is situated between the base 1232 and any lockwire extending within the lockwire lumen 1216. Accordingly, one or more constraining fibers can be lassoed around or otherwise coupled to the portion of the lockwire spanning the gap formed between the proximal and distal surfaces 1228 and 1230, as discussed below.

While the examples discussed above include a relief revolved about a portion of the olive 1200, in some examples, the lockwire exposure feature 1222 may be formed by simply boring into the olive 1200 an amount sufficient to expose the lockwire lumen 1216 and any lockwire extending within the lockwire lumen 1216. While such a bore is traditionally circular and uniform, it should be appreciated that it need not be. Likewise, in some examples, the relief may be formed in the exterior surface 1226 along a longitudinal length of the olive 1200 (see e.g., FIGS. 2A-2B).

Referring again to FIG. 1C, as shown, the lockwire exposure feature 1222 bisects the lockwire lumen 1216 such that the lockwire lumen 1216 includes a proximal section 1218 and a distal section 1220. Generally, the proximal section 1218 of the lockwire lumen 1216 extends between the proximal surface 1228 and one of the proximal end 1204 and the proximal taper portion 1210. The distal section 1220 of the lockwire lumen 1216 generally extends between the distal surface 1230 and one of the distal end 1206 and the distal taper portion 1212. However, as mentioned above, the lockwire lumen may terminate at some point interior of the olive 1200 and thus not extend through the olive 1200 entirely.

In various examples, the lockwire 1300 is a longitudinally extending structure configured to engage the olive 1200 such that one or more medical devices can be coupled to the lockwire 1300. In some examples, the lockwire 1300 can secure one or more steering lines to the olive 1200. In other examples, the lockwire 1300 can additionally or alternatively secure one or more medical devices and/or one or more constraining fibers (or wires) to the olive 1200.

In some examples, the lockwire 1300 extends from a treatment side inside a patient's vasculature to a proximal position outside of the body of the patient. In some examples, the lockwire 1300 extends adjacent the elongate element 1100. In some examples, the lockwire 1300 extends through in interior lumen of the elongate element 1100. For instance, in some examples, the lockwire 1300 extends through a lockwire lumen of the elongate element 1100. That is, in some examples, the elongate element 1100 includes a lockwire lumen in addition to one or more other lumens, such as working lumens. In some examples, the lockwire extends through the one or more working lumens of the elongate element 1100.

In some examples, as explained further below, the lockwire 1300 releasably couples one or more medical devices, constraining fibers (or wires), and/or steering lines to the olive 1200. Any manner in which the lockwire 1300 can interact with such medical devices, constraining fibers (or wires), and/or steering lines to maintain a releasable coupling therebetween is within the scope of the present disclosure.

In various examples, the lockwire 1300 can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Further, the lockwire 1300 can also be formed from high strength polymer fibers such as ultra-high molecular weight polyethylene fibers (e.g., Spectra®, Dyneema Purity®, etc.) or aramid fibers (e.g., Technora®, etc.). Any material that can provide sufficient engagement with and secure the medical devices, constraining fibers, and/or steering lines to the olive 1200 is within the scope of the present disclosure.

In some examples, as mentioned above, the medical device delivery system 1000 operates to maintain a position of a medical device along the medical device delivery system 1000 during delivery and/or deployment of the medical device at a treatment region or site. It should be appreciated that minimizing or otherwise constraining the medical device against longitudinal movement along the medical device delivery system facilitates accurate and reliable deployment of the medical device at a treatment region or site.

Figure 3C:
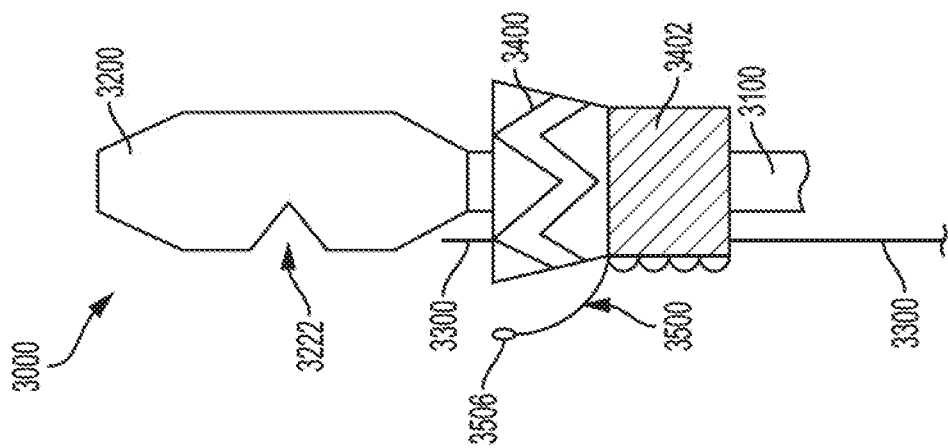
FIGS. 3A-3C illustrate a medical device delivery system consistent with various aspects of the present disclosure.
Figure 3B:
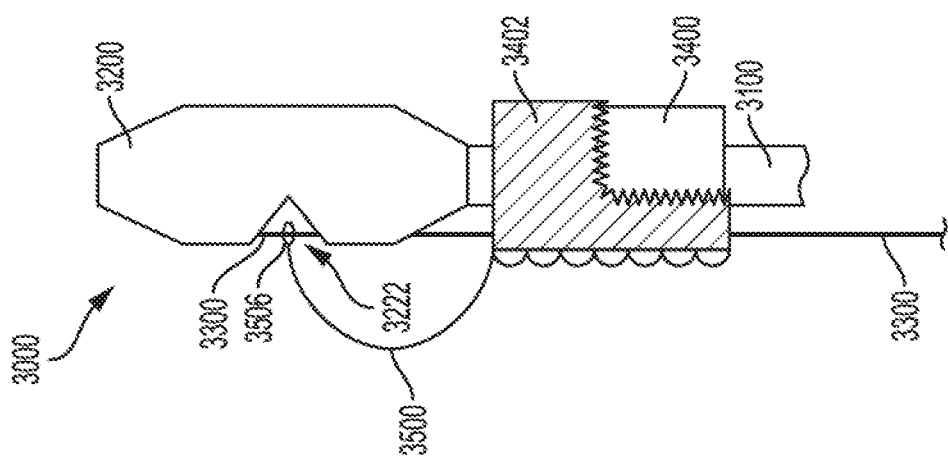
Figure 3A:
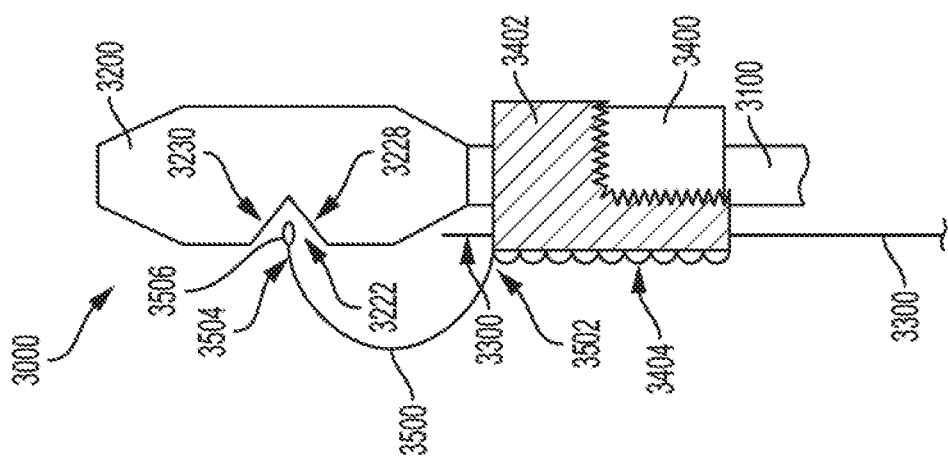

Turning now to FIGS. 3A-3C, a medical device delivery system 3000 is illustrated as including an elongate element 3100, an olive 3200, and a lockwire 3300. In some examples, the medical device delivery system 3000 further includes a control system (not illustrated). For example, a control system may be coupled to a proximal end of one or more of the elongate element 3100 and/or the lockwire 3300. In some examples, the control system may operate to advance or retract the lockwire 3300 or deflect the olive 3200 as those of skill will appreciate.

As shown, a medical device 3400 and a deployment sheath 3402 are mounted on the medical device delivery system 3000 (FIGS. 3A and 3B are illustrated with a portion of the deployment sheath 3402 removed such that a portion of the medical device 3400 is pictured). A constraining element, such as constraining fiber 3500 is illustrated as extending from a distal end of the medical device/sheath to the lockwire 3300. As explained in greater detail below, the constraining fiber 3500 operates to couple the medical device 3400 and/or the deployment sheath 3402 to the medical device delivery system 3000 such that the medical device 3400 and/or the deployment sheath 3402 are constrained against longitudinal movement along the medical device delivery system during delivery and/or deployment of the medical device 3400 at the target site or region.

The elongate element 3100, the olive 3200, and the lockwire 3300 are consistent with the various elongate elements, olives, and lockwires discussed herein. It should be appreciated that while the examples below refer to the constraining element as a constraining fiber 3500, such reference should not be interpreted as limiting. For instance, it should be appreciated that the constraining element may be a structure that is suitable for being placed in tension, compression, or tension and compression.

In various examples, the medical device 3400 is any suitable structure configured to provide treatment to the vasculature. For instance, the medical device can be any suitable medical device including, for example, a stent, a stent graft, a filter, a valve, a bifurcated stent, an occluder, a drug-delivering device, such as a drug-eluting balloon and/or stent, an oncology therapy, a pressure flow monitor, an energy transmission device, a spacer, an optical device, a marker, a sheath, and/or any other similar endoluminally deliverable device.

The medical device may be comprised of a shape-memory material, such as nitinol, or may be comprised of other materials, self-expandable or otherwise expandable (e.g., with a conventional balloon catheter or spring mechanism), such as various metals (e.g., stainless steel), alloys and polymers.

The deployment sheath generally covers the medical device and restrains the medical device toward an outer peripheral dimension or delivery configuration suitable for endoluminal delivery as those of skill in the art should appreciate. In various examples, the deployment sheath is any suitable sheath or sleeve that wraps around and constrains the medical device toward a delivery configuration for endoluminal delivery. The deployment sheath is flexible so that it generally conforms to the shape of the medical device and is sufficiently strong to restrain the medical device toward a delivery configuration during deployment to the treatment site. In various examples, a deployment sheath can be axially displaced or removed to reveal the medical device and allow expansion of the medical device at the treatment site.

In various examples, the deployment sheath can be made from a flexible film and comprise a series of holes, openings, passages, or eyelets defined along generally opposite sides of (or an entire periphery of) the sheath. In various examples, the sheath can be wrapped around and cover the medical device, and a release line, stitch, or constraining fiber can be threaded through the holes to compress and/or restrain the medical device toward a delivery configuration. During deployment, the release line, stitch, or constraining fiber, un-threads, or is otherwise released from the holes to release the deployment sheath and allow the medical device to expand. In some examples, the deployment sheath may be proximally withdrawn from the medical device after deployment of the medical device.

In various examples, the deployment sheath can be made of any suitable material, including for example, a fluoropolymer such as ePTFE. Alternatively, or in combination with a fluoropolymer, the deployment sheath can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk can be included in the deployment sheath.

As shown in FIG. 3A, the medical device 3400 is covered or constrained by a deployment sheath 3402 such that the medical device 3400 and the deployment sheath 3402 are mounted on the medical device delivery system 3000. In some examples, the medical device 3400 and/or the deployment sheath 3402 comprise one or more mechanisms that may serve as attachment points or vehicles for coupling the medical device 3400 and or deployment sheath 3402 to the medical device delivery system 3000. As mentioned above, these attachment points or vehicles may be holes or stitches incorporated into the deployment sheath. For example, as illustrated in FIG. 3A, the deployment sheath 3402 includes a stitch portion 3404, such as a chain stitch. As shown, a proximal end 3502 of the constraining fiber 3500 is coupled or otherwise incorporated into the deployment sheath 3402. In some examples, the constraining fiber 3500 forms a portion of the stitch portion 3404. In some examples, the constraining fiber 3500 is coupled to or otherwise woven through one or more of the stitches of the stitch portion 3404. For instance, the constraining fiber 3500 may be routed through the top or distal-most stitch and then to the lockwire 3300 such that, until the constraining fiber 3500 is decoupled from the lockwire 3300, the constraining fiber 3500 operates to prevent premature unlacing of the chain stitch (and thus premature deployment of the medical device 3400). In some examples, after the constraining fiber 3500 is decoupled from the lockwire 3300, the constraining fiber 3500 can be removed from the chain stitch such that the chain stitch can unlace and the medical device 3400 can be deployed. Thus, in such examples, the constraining fiber 3500 serves a dual purpose of maintaining a position of the medical device 3400 along the medical device delivery system 3000 (device fixation) and locking the stitch, although examples with one or the other feature are also contemplated.

It should be appreciated that device fixation provides for a consistent position and length of the medical device as it is collapsed and loaded onto the elongate element (crush) and during its deployment at the target region. Additionally, device fixation provides for a consistent position of the medical device relative to the elongate element and/or olive as the medical device delivery system is bent and/or manipulated as it is advanced through the vasculature.

In some examples, the constraining fiber 3500 is additionally or alternatively coupled to one or more of holes formed in the deployment sheath, such as one or more of the holes formed by the stitches of the stitch portion 3404. However, the constraining fiber 3500 may be coupled to one or more holes formed in the deployment sheath 3402 that are not associated with the stitch portion 3404. Likewise, the constraining fiber 3500 may be additionally or alternatively incorporated into the medical device.

In some examples, the distal end 3504 of the constraining fiber 3500 is configured to interface with the lockwire 3300. In some such examples, the constraining fiber includes a knob, an eyelet, a hole, or any other suitable attachment mechanism 3506 at its distal end 3504. The attachment mechanism 3506 is configured such that the lockwire 3300 can pass through or otherwise engage the attachment mechanism 3506 to releasably couple the constraining fiber 3500 to the lockwire 3300.

In some examples, as discussed further below, the lockwire 3300 is configured to be advanced into the lockwire lumen (described above but not illustrated in FIGS. 3A-3C) and across the gap formed by the lockwire exposure feature 3222. In the illustrated example of FIG. 3A, the constraining fiber 3500 can be coupled with the lockwire 3300 by distally advancing the lockwire 3300 from its position proximal to the olive 3200 such that the lockwire 3300 is advanced through the proximal portion of the lockwire lumen, across the gap formed by the lockwire exposure feature 3222, through the attachment mechanism 3506 of the constraining fiber 3500 an into the distal portion of the lockwire lumen.

As shown in FIG. 3A, the constraining fiber 3500 is configured to extend between the deployment sheath 3402 and/or the medical device 3400 and the lockwire exposure feature 3222 of the olive 3200 such that the constraining fiber 3500 can interface with the portion of the lockwire 3300 extending through the olive 3200 that is exposed by the lockwire exposure feature 3222. FIG. 3A illustrates the medical device 3400 and the deployment sheath 3402 mounted on the elongate element 3100 prior to the lockwire 3300 being inserted into the lockwire lumen (described above but not illustrated in FIGS. 3A-3C).

In various examples, coupling the constraining fiber 3500 to the lockwire 3300 includes positioning the attachment mechanism 3506 of the constraining fiber 3500 within the gap formed by 3222 such that, as the lockwire 3300 traverses the gap, the lockwire 3300 passes through the attachment mechanism 3506 of the constraining fiber 3500. Specifically, in some examples, as the lockwire 3300 is distally advanced from the proximal portion of the lockwire lumen to the distal portion of the lockwire lumen (such as during a proximal-to-distal insertion and advancement of the lockwire into the olive 3200), the lockwire 3300 exits the proximal portion of the lockwire lumen and traverses the gap separating the proximal portion of the lockwire lumen from the distal portion of the lockwire lumen. The attachment mechanism 3506 of the constraining fiber 3500 is situated such that during this traversal of the gap by the lockwire 3300 and before the lockwire 3300 enters the distal portion of the lockwire lumen, the distal end of the lockwire 3300 passes through the attachment mechanism 3506. With the lockwire 3300 extending through the attachment mechanism 3506, the constraining fiber 3500 is coupled to or otherwise restrained by the lockwire 3300. As discussed in greater detail below, decoupling the constraining fiber 3500 from the lockwire 3300 is generally the reverse procedure of coupling the constraining fiber 3500 to the lockwire 3300.

In some examples, the lockwire is recoupleable to the olive after it has been decoupled therefrom. That is, in some examples, the lockwire is reinsertable into the lockwire lumen. In some examples, the constraining fiber is reattachable to a reinserted lockwire. However, in some other examples, the lockwire is not recoupleable to the olive after it has been decoupled therefrom. Likewise, in some examples, after decoupling the constraining fiber from the lockwire, the constraining fiber is not recoupleable to the lockwire.

It should be appreciated that, while FIGS. 3A-3C illustrate the lockwire 3300 being inserted into the olive 3200 in a proximal-to-distal direction, other examples may include inserting the lockwire 3300 into the olive 3200 in a distal-to-proximal. During a distal-to-proximal insertion and advancement of the lockwire 3300 into the olive 3200, after the lockwire 3300 exists the distal portion of the lockwire lumen and before the lockwire 3300 enters the proximal portion of the lockwire lumen, the distal end of the lockwire 3300 passes through the attachment mechanism 3506. In such examples, decoupling the constraining fiber 3500 from the lockwire 3300 is generally the reverse procedure.

FIG. 3B illustrates the interface between the lockwire 3300 and the constraining fiber 3500 with the lockwire 3300 received in both the proximal and distal portions of the lockwire lumen after the lockwire 3300 has passed through the attachment mechanism 3506 of the constraining fiber 3500. With the constraining fiber 3500 coupled to the lockwire 3300 as shown in FIG. 3B, the deployment sheath 3402 and the medical device 3400 are constrained against translating axially (and in particular, proximally) relative to the elongate element 3100 during delivery and deployment of the medical device 3400.

In some examples, the constraining fiber 3500 is operable to apply a tensile force to the medical device 3400 and/or the deployment sheath 3402 should the medical device 3400 and/or the deployment sheath 3402 tend to translate proximally along the elongate element 3100. Generally, such tensile force is operable to counteract proximal translation.

In some examples, with the distal end 3504 of the constraining fiber 3500 coupled with or otherwise retained by the portion of the lockwire exposed by the lockwire exposure feature 3222, the distal end 3504 of the constraining fiber 3500 is constrained against axial translation along the lockwire 3300 and constrained against radial translation away from the olive 3200. Specifically, in some examples, the of the attachment mechanism 3506 of the constraining fiber 3500 is constrained such that axial translation along the lockwire 3300 is limited to travel between a distal end of the proximal portion of the lockwire lumen and a proximal end of the distal portion of the lockwire lumen (i.e., between the proximal and distal surfaces 3228 and 3230 of the lockwire exposure feature 3222). That is, the attachment mechanism 3506 of the constraining fiber 3500 is limited to translating along the portion of the lockwire 3300 that is exposed by the lockwire exposure feature 3222. In addition, the extension of the lockwire 3300 through the attachment mechanism 3506 of the constraining fiber 3500 forms a hitch that prevents the constraining fiber 3500 from being radially withdrawn from the lockwire 3300.

With a distal end 3504 of the constraining fiber 3500 coupled to the olive 3200 and a proximal end 3502 of the constraining fiber 3500 coupled to the deployment sheath 3402, the constraining fiber 3500 operates to constrain the deployment sheath 3402 against longitudinal translation along the elongate element 3100 upon which the medical device 3400 and the deployment sheath 3402 are mounted, as mentioned above. Those of skill in the art should appreciate that while the constraining fiber 3500 in this illustrated example is not directly coupled to the medical device 3400, the friction between the deployment sheath 3402 and the medical device 3400 operates to maintain a relative position between the medical device 3400 and the deployment sheath 3402.

In some examples, decoupling the constraining fiber 3500 from the lockwire 3300 involves withdrawing the lockwire 3300 from at least a portion of the lockwire lumen, which, as mentioned above, generally involves the reverse process of inserting the lockwire 3300 into the lockwire lumen. FIG. 3C illustrates the lockwire 3300 having been proximally withdrawn from the lockwire lumen of the olive 3200 and the attachment feature 3506 of the constraining fiber 3500. It should be appreciated that while the lockwire 3300 is illustrated in FIG. 3C as having been withdrawn from the lockwire lumen entirely, in some examples, the lockwire 3300 need not be withdrawn from the lockwire lumen entirely to facilitate decoupling of the constraining fiber 3500. Instead, in some examples, the lockwire 3300 need only be withdrawn to the extent that the distal end of the lockwire 3300 clears the attachment mechanism 3506 of the constraining fiber 3500.

Generally, where the lockwire 3300 is inserted into the lockwire lumen of the olive in a proximal-to-distal manner, the lockwire 3300 need only be withdrawn from the distal portion of the lockwire lumen and the attachment mechanism 3506 of the constraining fiber 3500. Thus, in some examples, the constraining fiber 3500 may be decoupled from the lockwire 3300 while the lockwire remains inserted in (or even through) the proximal portion of the lockwire lumen. Likewise, where the lockwire 3300 is inserted into the lockwire lumen of the olive 3200 in a distal-to-proximal manner, the constraining fiber 3500 may be decoupled from the lockwire 3300 by distally withdrawing the lockwire 3300 from the proximal portion of the lockwire lumen and the attachment mechanism 3506.

As shown in FIG. 3C, with the constraining fiber 3500 decoupled from the lockwire 3300, the medical device 3400 and the deployment sheath 3402 are no longer constrained against axial translation along the elongate element 3100 by the constraining fiber 3500. Accordingly, as shown in FIG. 3C, with the constraining fiber 3500 decoupled from the lockwire 3300, the deployment sheath 3402 is removable from the medical device 3400 such that the medical device 3400 can be deployed. In some examples, as discussed above, the medical device is expanded as it is deployed.

Figure 4A:
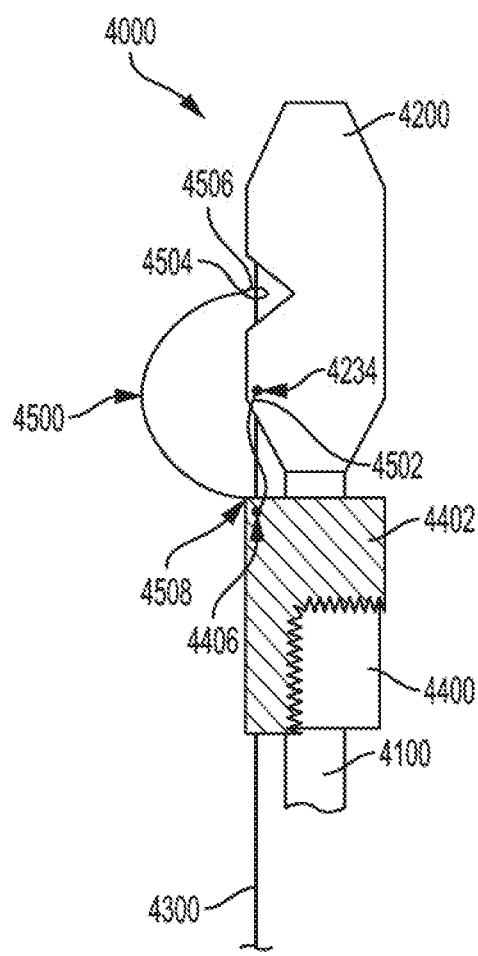
FIGS. 4A and 4B illustrate a medical device delivery system consistent with various aspects of the present disclosure.
Figure 4B:
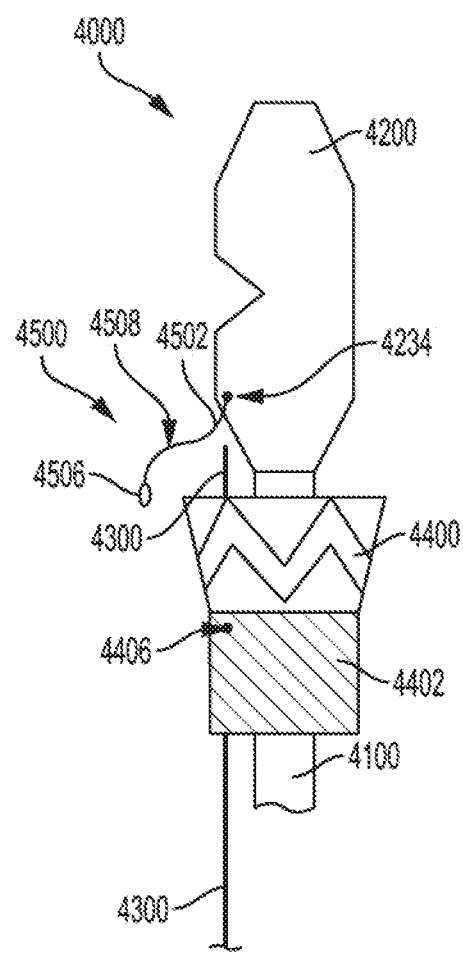

While some of the above-discussed examples include coupling a proximal end of the constraining fiber to one or both of the deployment sheath and the medical device, in some examples, the proximal end of the constraining fiber is coupled to the olive of the medical device deployment system. Turning now to FIGS. 4A and 4B, a medical device delivery system 4000 is illustrated as including an elongate element 4100, an olive 4200, and a lockwire 4300. As shown, a medical device 4400 and a deployment sheath 4402 are mounted on the medical device delivery system 4000 and releasably coupled thereto by a constraining element, such as constraining fiber 4500 (FIG. 4A is illustrated with a portion of the deployment sheath 4402 removed such that a portion of the medical device 4400 is pictured). As explained in greater detail below, the constraining fiber 4500 operates to couple the medical device 4400 and/or the deployment sheath 4402 to the medical device delivery system 4000 such that the medical device 4400 and/or the deployment sheath 4402 are constrained against longitudinal movement along the medical device delivery system 4000 during delivery and/or deployment of the medical device 4400 at the target site or region.

The elongate element 4100, the olive 4200, the lockwire 4300 are consistent with the various elongate elements, olives, and lockwires discussed herein. It should be appreciated that while the examples below refer to the constraining element as a constraining fiber 4500, such reference should not be interpreted as limiting. For instance, it should be appreciated that the constraining element may be a structure that is suitable for being placed in tension, compression, or tension and compression.

As shown in FIG. 4A, the medical device 4400 is covered or constrained by a deployment sheath 4402 such that the medical device 4400 and the deployment sheath 4402 are mounted on the medical device delivery system 4000. In some examples, the medical device 4400 and/or the deployment sheath 4402 comprise one or more mechanisms that may serve as attachment points or vehicles for coupling the medical device 4400 and or deployment sheath 4402 to the medical device delivery system 4000. As mentioned above, these attachment points or vehicles may be holes or stitches incorporated into the deployment sheath.

In the illustrated examples of FIGS. 4A and 4B, the deployment sheath 4402 includes at least one constraining fiber aperture, such as constraining fiber aperture 4406. In some examples, the constraining fiber aperture 4406 is configured to have the constraining fiber 4500 passed therethrough in a manner that couples the deployment sheath 4402 to the medical device delivery system 4000, as explained in greater detail below.

As shown in FIGS. 4A and 4B, like the constraining fiber 3500, the constraining fiber 4500 is configured to interface with the lockwire 4300. Specifically, as shown, the constraining fiber includes attachment mechanism 4506 (e.g., a knob, an eyelet, a hole, or any other suitable attachment mechanism) at its distal end 4504. Like the attachment mechanism 3506, attachment mechanism 4506 is configured such that the lockwire 4300 can pass through the attachment mechanism 4506 to couple the constraining fiber 4500 to the lockwire 4300. However, unlike the proximal end 3502 of the constraining fiber 3500, the proximal end 4502 of the constraining fiber 4500 is coupled to the olive 4200.

Accordingly, as illustrated in FIG. 4A, the constraining fiber 4500 is configured to extend from the olive 4200 and through the deployment sheath 4402 and/or the medical device 4400 such that a distal end 4504 and/or an attachment mechanism 4506 of the constraining fiber 4500 is operable to be coupled to a portion of the lockwire 4300 inserted into the lockwire lumen of the olive 4200 and exposed by the lockwire exposure feature 4222. In various examples, the distal end 4504 and/or the attachment mechanism 4506 of the constraining fiber 4500 interfaces with the lockwire 4300 in a similar manner as discussed above with respect to the manner in which the distal end 3504 and/or the attachment mechanism 3506 of the constraining fiber 3500 interfaces with the lockwire 3300. The proximal end 4502 of the constraining fiber 4500 is coupled to the olive 4200 as mentioned above. In various examples, the proximal end 4502 of the constraining fiber 4500 may by tied, adhered, welded, screwed or attached via one or more fasteners to the olive 4200, as mentioned above.

FIG. 4A illustrates the medical device 4400 and the deployment sheath 4402 mounted on the elongate element 4100 with the lockwire 4300 extending through the attachment mechanism 4506 of the constraining fiber 4500 and into the distal portion of the lockwire lumen (described above but not illustrated in FIGS. 4A and 4B). Accordingly, as shown, the constraining fiber 4500 is releasably coupled to the lockwire 4300. Generally, with the proximal end 4502 of constraining fiber 4500 coupled to the olive 4200 and the distal end 4504 of the constraining fiber 4500 coupled to the lockwire 4300, an intermediate portion 4508 of the constraining fiber 4500 engages the medical device 4400 and/or the deployment sheath 4402. As illustrated in FIG. 4A, the intermediate portion of the constraining fiber 4500 passes through the constraining fiber aperture 4406 of the deployment sheath 4402. In some examples, the intermediate portion 4508 may be looped around or looped through the constraining fiber aperture 4406 of the deployment sheath 4402. In some examples, the intermediate portion of the constraining fiber 4500 additionally or alternatively similarly passes through (or is looped around and through) a constraining fiber aperture or some other engagement feature of the medical device 4400.

Thus, the configuration illustrated in FIG. 4A provides that the deployment sheath 4402 and/or the medical device 4400 are constrained against translating axially (and in particular, proximally) relative to the elongate element 4100 upon which the deployment sheath 4402 and the medical device 4400 are mounted. For instance, as similarly discussed above with respect to constraining fiber 3500, in some examples, the constraining fiber 4500 is operable to apply a tensile force to the medical device 3400 and/or the deployment sheath 3402 to counteract a tendency of the medical device 3400 and the deployment sheath 3402 to translate proximally along the elongate element 3100.

In some examples, the constraining fiber 4500 is decoupleable from the lockwire 4300 in a manner similar to the manner in which the constraining fiber 3500 is decoupled from the lockwire 3300. FIG. 4B illustrates the lockwire 4300 having been proximally withdrawn from the lockwire lumen of the olive 4200 such that the lockwire 4300 is withdrawn from the attachment feature 4506 of the constraining fiber 4500. With the constraining fiber 4500 decoupled from the lockwire 4300, the medical device 4400 and the deployment sheath 4402 are no longer constrained against axial translation along the elongate element 4100 by the constraining fiber 4500. Accordingly, as shown in FIG. 4B, with the constraining fiber 4500 decoupled from the lockwire 4300, the deployment sheath 4402 is removable from the medical device 4400 such that the medical device 4400 can be deployed.

Turning now to FIGS. 5A and 5B, a medical device delivery system 5000 is illustrated as including an elongate element 5100, an olive 5200, a lockwire 5300, a constraining element or steering element, such as steering fiber 5500, and a delivery catheter 5600. The elongate element 5100, the olive 5200, and the lockwire 5300 are consistent with the various elongate elements, olives, and lockwires discussed herein. It should be appreciated that while the examples below refer to the constraining element as a constraining fiber 5500, such reference should not be interpreted as limiting. For instance, it should be appreciated that the constraining element may be a structure that is suitable for being placed in tension, compression, or tension and compression. Thus, in some examples, the constraining element may be a constraining wire that is suitable to be placed in tension and/or compression. Likewise, in some examples, the lockwire may be a fiber and/or a wire in that may be placed in tension and compression, while in some other examples the lockwire may be placed only in tension.

Generally, the steering fiber 5500 allows for selective bending of the elongate element 5100 within the vasculature. In such configurations, tension can be applied to the steering fiber 5500 to cause the elongate element 5100 to bend as those of skill in the art should appreciate. Bending the elongate element 5100 can, among other things, help facilitate conformity of the medical device delivery system 5000 to curvatures in the vasculature of a patient which facilitates advancement of the medical device delivery system 5000 through curved regions of vasculature. Thus, such a configuration can be useful during delivery of the medical device delivery system 5000 to the target region or site.

In some examples, the steering fiber 5500 passes through the delivery catheter 5600 and is releasably coupled to the olive 5200. In some examples, the steering fiber 5500 includes an attachment mechanism 5506 which is similar to the attachment mechanism 3506 of the constraining fiber 3500 described and illustrated herein. Thus, consistent with the examples discussed above, the steering fiber 5500 is configured to interface with the portion of the lockwire 5300 inserted within the lockwire lumen (described above but not illustrated in FIGS. 5A and 5B) of the olive 5200 that is exposed by the lockwire exposure feature 5222.

In some examples, the steering fiber 5500 is of a similar material and construction as the constraining fibers discussed above. In some examples, the steering fiber 5500 can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Further, the steering fiber 5500 can also be formed from high strength polymer fibers such as ultra high molecular weight polyethylene fibers (e.g., Spectra®, Dyneema Purity®, etc.) or aramid fibers (e.g., Technora®, etc.). However, any material that can be used to bend and/or steer the elongate element or otherwise cause the olive 5200 to deflect is within the scope of the present disclosure.

FIG. 5B illustrates the medical device delivery system 5000 in a deflected configuration (FIG. 5A illustrates the medical device delivery system 5000 in a nondeflected configuration). Thus, by configuring the constraining fiber as a steering fiber, the medical device delivery system 5000 is transitionable between deflected and nondeflected (or steered and nonsteered) states or configurations.

Similar to the various other examples illustrated and describe herein, the steering fiber 5500 is removably coupled to the olive 5200. Such a configuration provides for a versatile medical device delivery system 5000 and interchangeability. For example, the illustrated example of FIGS. 5A and 5B may be combinable with the other examples illustrated and discussed herein. For example, a medical device delivery system may include a plurality of constraining fibers coupled to the portion of the lockwire inserted within the lockwire lumen that is exposed by the lockwire exposure feature. In some such examples, a first of the constraining fibers may operate to maintain a position of a medical device and/or a deployment sheath along an elongate element, while a second constraining fiber operates as a steering fiber that facilitates delivery of the medical device delivery system to the treatment region within the vasculature.

Moreover, such a configuration provides for selective decoupling of one or more of the plurality of constraining fibers from the lockwire. In some examples, the steering fiber may be decoupleable from the lockwire without decoupling the constraining fiber from the lockwire. For instance, in some examples, the lockwire may be withdrawn through the lockwire lumen a degree sufficient to enable decoupling of the steering fiber but insufficient to enable decoupling of the constraining fiber. In some examples, the lockwire may be withdrawn through the lockwire lumen a degree sufficient to enable decoupling of both the steering fiber and the constraining fiber but only the steering fiber is decoupled from the lockwire, after which the lockwire is readvanced to a position within the lockwire lumen that prohibits decoupling of the constraining fiber that remains coupled to the lockwire. These and other examples are likewise combinable with the medical device delivery systems discussed below.

Figure 6A:
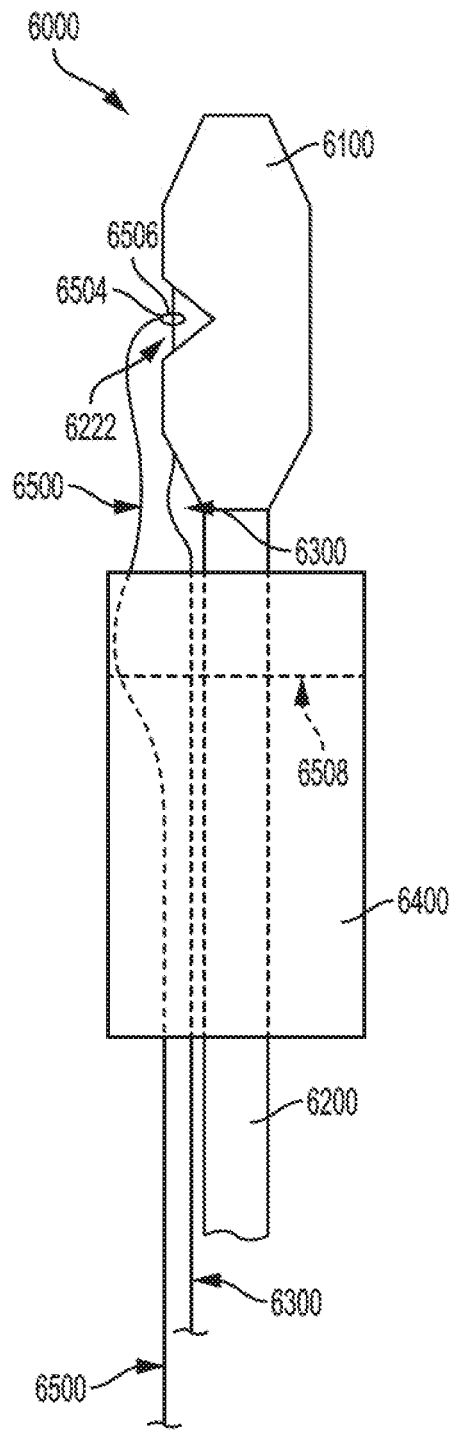
FIGS. 6A and 6B illustrate a medical device delivery system consistent with various aspects of the present disclosure.
Figure 6B:
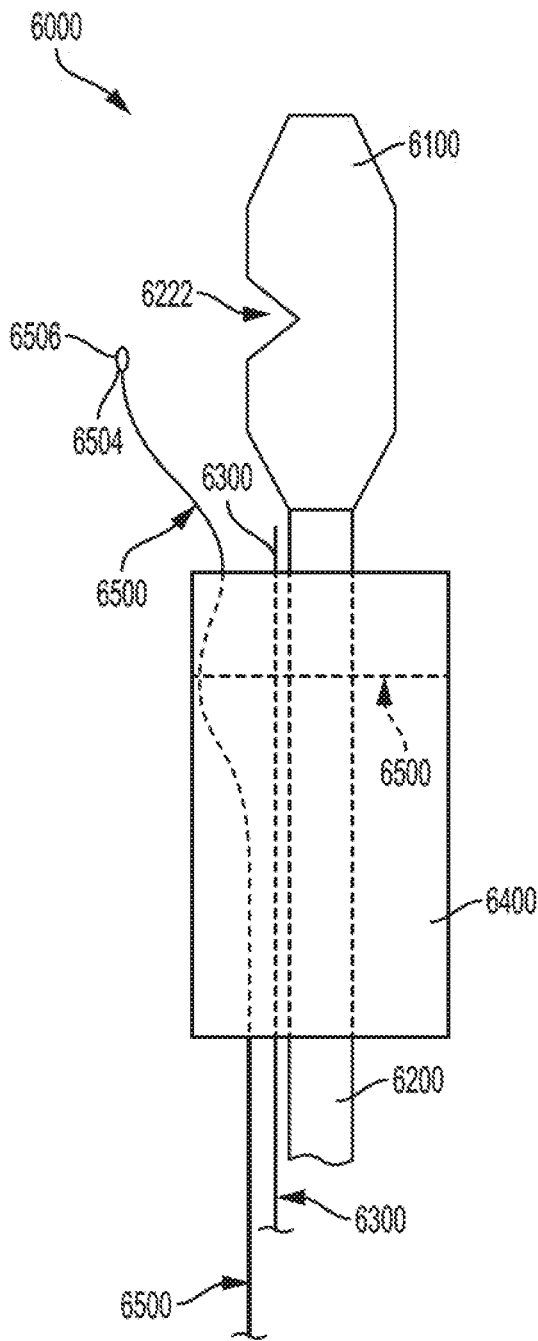

Turning now to FIGS. 6A and 6B, a medical device delivery system 6000 is illustrated as including an elongate element 6100, an olive 6200, a lockwire 6300, and a constraining element, such as constraining fiber 6500. The elongate element 6100, the olive 6200, the lockwire 6300, and the constraining fiber 6500 are consistent with the various elongate elements, olives, lockwires, and constraining fibers discussed herein. It should be appreciated that while the examples below refer to the constraining element as a constraining fiber 6500, such reference should not be interpreted as limiting. For instance, it should be appreciated that the constraining element may be a structure that is suitable for being placed in tension, compression, or tension and compression.

As illustrated, the constraining fiber 6500 is configured such that the distal portion 6504 and/or the attachment mechanism 6506 is coupled with the portion of the lockwire 6300 inserted within the lockwire lumen (discussed above but not illustrated in FIGS. 6A and 6B) and exposed by the lockwire exposure feature 6222. The distal end 6504 of the constraining fiber 6500 extends from an intermediate portion 6508 of the lockwire 6500 that is coupled with the medical device 6400. As discussed in greater detail below, the intermediate portion 6508 of the constraining fiber 6500 is coupled with the medical device 6400 such that the constraining fiber 6500 can operate to selectively reduce a cross section of a portion of the medical device 6400. The intermediate portion 6508 of the constraining fiber 6500 extends from a proximal end of the constraining fiber 6500 (not illustrated in FIGS. 6A and 6B), such as outside the body, for example.

As illustrated in FIGS. 6A and 6B, the constraining fiber 6500 is coupled to the medical device 6400. Specifically, the constraining fiber 6500 is laced around a periphery or circumference of the medical device 6400. Generally, the constraining fiber 6500 is laced about the periphery of the medical device such that the constraining fiber 6500 can operate to selectively reduce a cross section (such as a diameter) or otherwise radially collapse a portion of the medical device 6400 in and around or proximate to where the constraining fiber 6500 is coupled to the medical device 6400 (e.g., the internal periphery of the inner lumen of the medical device 6400). In some examples, the constraining fiber 6500 is laced on an internal periphery of the medical device 6400. In some examples, the constraining fiber 6500 is additionally or alternatively laced about an external periphery of the medical device 6400. In some examples, the constraining fiber 6500 extends within an integrated constraining lumen or other circumferentially extending lumen, as discussed in greater detail below. In some examples, the constraining fiber 6500 is routed or laced about an entire periphery of the medical device 6400. In other examples, the constraining fiber 6500 is routed or laced about a portion of less than the entire periphery of the medical device 6400.

In some examples, by coupling the distal end 6504 and/or the attachment mechanism 6506 of the constraining fiber 6500 to the lockwire 6300, a tension can be applied to the constraining fiber 6500 without removing the constraining fiber 6500 from the medical device delivery system 6000. Specifically, because the distal end 6504 of the constraining fiber 6500 is coupled to the lockwire 6300 at the olive 6200, the distal end 6504 is constrained against axial translation (see discussion above) as tension is applied to the proximal end of the constraining fiber 6500. Thus, the intermediate portion 6508 of the constraining fiber 6500 laced about the medical device 6400 constricts to reduce the cross section of the portion of the medical device 6400 about which the intermediate portion 6508 is laced.

Specifically, in some examples, as tension is applied to the constraining fiber 6500 (either from a proximal or distal end of the constraining fiber), a length of the constraining fiber 6500 routed about the periphery of the medical device 6400 is reduced such that the peripheral portion of the medical device 6400 about which the constraining fiber 6500 is routed is reduced. In some examples, the reduction in cross section of the medical device 6400 is proportional to the reduction in length of the portion of the constraining fiber 6500 that is routed about the periphery of the medical device 6400. Thus, as the length of the portion of the constraining fiber 6500 that is routed about the periphery of the medical device 6400 decreases, so decreases the cross sectional area of the medical device 6400 in that region.

By providing a mechanism that allows for selectively reducing the cross section of the medical device, users can avoid premature anchoring of the medical device. In some examples, such versatility operates to avoid damaging a vessel where a medical device requires repositioning after initial deployment.

Because the constraining fiber 6500 is removably coupled to the lockwire 6300, after the medical device 6400 is properly oriented and deployed, the constraining fiber 6500 can be decoupled from the lockwire 6300 (consistent with the examples discussed herein). In some examples, after properly aligning the medical device 6400, the tension applied to the constraining fiber 6500 is released such that the medical device 6400 can adopt a natural configuration within the portion of the vasculature in which it is situated. In some examples, after releasing the tension on the constraining fiber 6500 the lockwire 6300 is withdrawn from the lockwire lumen of the olive 6200 such that the constraining fiber 6500 can be decoupled from the lockwire (see discussion above).

FIG. 6B illustrates a configuration wherein the constraining fiber 6500 is decoupled from the lockwire 6300. As shown, the lockwire 6300 has been proximally withdrawn from the lockwire lumen of the olive 6200 and the distal end 6504 constraining fiber 6500 is free from the lockwire 6300. In some examples, with the constraining fiber 6500 free (i.e., not coupled to the lockwire 6300), the constraining fiber 6500 can be withdrawn from the medical device delivery system 6000. In some examples, the constraining fiber 6500 can be withdrawn and decoupled from the medical device 6400. In some such examples, as tension is applied to the proximal end of the constraining fiber 6500, the free distal end 6504 is drawn away from the olive 6200 and through the medical device 6400 and out of the body. In some other examples, only a portion of the constraining fiber 6500 is removed from the body. For instance, in some examples, the constraining fiber 6500 is configured to bio-disintegrate and thus may remain in the body after deployment of the medical device 6400 and removal of the other components of the medical device delivery system 6000.

Turning now to FIG. 7, a medical device delivery system 7000 is illustrated as including an elongate element 7100, an olive 7200, a lockwire 7300, and a constraining element, such as constraining fiber 7500. The elongate element 7100, the olive 7200, the lockwire 7300, and the constraining fiber 7500 are consistent with the various elongate elements, olives, lockwires, and constraining fibers discussed herein. It should be appreciated that while the examples below refer to the constraining element as a constraining fiber 7500, such reference should not be interpreted as limiting. For instance, it should be appreciated that the constraining element may be a structure that is suitable for being placed in tension, compression, or tension and compression.

As illustrated, the constraining fiber 7500 is configured such that the distal portion 7504 and/or the attachment mechanism 7506 are coupled with the portion of the lockwire 7300 inserted within the lockwire lumen (discussed above but not illustrated in FIG. 7) and exposed by the lockwire exposure feature 7222. The distal end 7504 of the constraining fiber 7500 extends from an intermediate portion 7508 of the constraining fiber 7500 that is coupled with the medical device 7400. In some examples, the intermediate portion 7508 of the constraining fiber 7500 is coupled with the medical device 7400 such that the constraining fiber 7500 can operate to selectively reduce a cross section of a portion of the medical device 7400, as discussed above. In some examples, the intermediate portion 7508 of the constraining fiber 7500 extends from a proximal end of the constraining fiber 7500 (not illustrated in FIG. 7).

As mentioned above, in various examples, as tension is applied to the constraining fiber 7500, a length of the constraining fiber 7500 routed about the periphery of the medical device 7400 is reduced such that the peripheral portion of the medical device 7400 about which the constraining fiber 7500 is route is reduced. Those of skill in the art will appreciate that the force applied to the medical device 7400 to induce such a tension is directed along the constraining fiber 7500. Thus, in various examples, it is beneficial to route the constraining fiber 7500 such that the force exerted on the medical device 7400 operates to efficiently and effectively reduce a cross section of a portion of the medical device 7400 while maintaining a longitudinal position of the medical device 7400 relative to the elongate element 7100.

As shown in FIG. 7, in some examples, the constraining fiber 7500 is routed through at least one alignment mechanism 7700. In some examples, the alignment mechanism 7700 includes one or more apertures or lumens through which the constraining fiber 7500 is routed. In other examples, the alignment mechanism 7700 additionally or alternatively includes one or more channels (i.e., open channels) or grooves through which the constraining fiber 7500 is routed. By routing the constraining fiber 7500 though one or more alignment mechanisms 7700, the constraining fiber 7500 can be routed such that the force exerted on the medical device 7400 by the constraining fiber 7500 is directed radially or semi-radially as opposed to longitudinally or substantially longitudinally. Directing the force radially or semi-radially has the effect of reducing the component of force that influences longitudinal translation of the medical device 7400 during delivery and deployment.

As shown in FIG. 7, the alignment mechanism 7700 is situated along the length of the constraining fiber 7500 between a proximal end of the constraining fiber 7500 and the intermediate portion of the constraining fiber 7500 that is coupled to or routed about the medical device 7400. Thus, in some examples, the constraining fiber 7500 is routed such that a first intermediate portion of the constraining fiber 7500 is routed through the alignment mechanism 7700 and a second intermediate portion of the constraining fiber 7500 is routed through the medical device 7400. In some examples, the first intermediate portion of the constraining fiber 7500 is proximal the second intermediate portion of the constraining fiber 7500 (see e.g., FIG. 7). However, as discussed in greater detail below, an alignment mechanism may additionally or alternatively be situated along the length of the constraining fiber 7500 between a distal end 7504 of the constraining fiber 7500 and the intermediate portion of the constraining fiber 7500 that is coupled to the medical device 7400.

In various examples, as tension is applied to the constraining fiber 7500, the portion of the constraining fiber 7500 extending between the alignment mechanism 7700 and the medical device 7400 exerts a force on the medical device 7400 that is directed along the length of the constraining fiber 7500 toward the alignment mechanism 7700. Thus, in some examples, applying tension to the constraining fiber 7500 causes the medical device 7400 to be drawn at least radially toward the alignment mechanism 7700. In some examples, this force may operate to further facilitate the reduction in cross section of the portion of the medical device about which the constraining fiber is laced or routed, as well as correct any unwanted rotation of the medical device about a longitudinal axis of the medical device delivery system. In some examples, such a force may also operate to maintain a position of the medical device along the longitudinal length of the medical device delivery system during delivery and/or deployment.

In some examples, the alignment mechanism 7700 is positioned such that the portion of the constraining fiber 7500 extending between the alignment mechanism 7700 and the medical device extends normal to (or substantially normal to) an interior surface of the medical device 7400. In some examples, the alignment mechanism 7700 is positioned such that the portion of the constraining fiber 7500 extending between the alignment mechanism 7700 and the medical device extends perpendicular to (or substantially perpendicular to) the longitudinal axis of the medical device delivery system 7000.

In some examples, the alignment mechanism 7700 is positioned such that the portion of the constraining fiber 7500 extending between the alignment mechanism 7700 and the medical device 7400 extends at some angle offset from being perpendicular to (or substantially perpendicular to) the longitudinal axis of the medical device delivery system 7000. In some examples, the constraining fiber 7500 extends from the alignment mechanism 7700 at an angle between forty-five (45) and ninety (90) degrees (or between ninety (90) and one-hundred-thirty-five (135) degrees) relative to the longitudinal axis of the medical device delivery system. However, it should be appreciated that an angle less than forty-five (45) degrees or greater than one-hundred-thirty-five (135) degrees may be selected without departing from the spirit or scope of the disclosure.

As shown in FIG. 7, the alignment mechanism 7700 is coupled to the elongate element 7100. In other examples, the alignment mechanism 7700 may be coupled to the olive 7200 or some other component of the medical device delivery system 7000. As shown, the alignment mechanism may be coupled to the olive or some other component of the medical device delivery system. The constraining fiber 7500 is routed such that a portion of the constraining fiber 7500 extends from a proximal end (not illustrated in FIG. 7) to the alignment mechanism 7700. The constraining fiber 7500 is routed through the alignment mechanism 7700 and to the medical device 7400 such that a portion of the constraining fiber 7500 extends between the alignment mechanism 7700 and the medical device 7400. As shown, the constraining fiber 7500 is routed through an aperture 7406 in the medical device 7400 and around a periphery of the medical device 7400 before extending to a position where the constraining fiber 7500 is coupled to the portion of the lockwire 7300 that is inserted in the lockwire lumen and exposed by the lockwire exposure feature 7222.

As shown in FIG. 7, the constraining fiber 7500 is routed about the periphery of the medical device 7400 such that, after extending about the periphery of the medical device 7400, the constraining fiber extends back through the aperture 7406 before extending to where it is coupled to the lockwire 7300. In some examples, the portion of the constraining fiber 7500 that extends to the lockwire 7300 overlaps or otherwise loops around the portion of the constraining fiber 7500 extending from the alignment mechanism 7700. For example, as shown in FIG. 7B, the portion 7512 of the constraining fiber 7500 that extends to the lockwire 7300 from the medical device 7400 passes beneath and around the portion 7510 of the constraining fiber 7500 extending to the medical device 7400 from the alignment mechanism 7700. In some such examples, the constraining fiber 7500 is looped around itself such that as tension is applied to the constraining fiber 7500, the portion of the constraining fiber 7500 that extends to the lockwire 7300 interferes with or otherwise entangles with the portion of the constraining fiber 7500 that extends from the alignment mechanism 7700. In some examples, looping or entangling the constraining fiber 7500 with itself operates to avoid the portions of the constraining fiber passing through the aperture 7406 of the medical device from binding against and tearing the edge or periphery of the aperture 7406 or another portion of the medical device 7400.

Turning back now to FIG. 7A, as discussed above, the distal end 7504 and/or the attachment mechanism 7506 are releasably coupled to the portion of the lockwire 7300 inserted into the lockwire lumen of the olive 7200 and exposed by the lockwire exposure feature 7222. As discussed above, by coupling the distal end 7504 and/or the attachment mechanism 7506 of the constraining fiber 7500, a tension can be applied to the constraining fiber 7500. Specifically, because the distal end 7504 of the constraining fiber 7500 is coupled to the lockwire at the olive 7200 and therefore constrained against axial translation (see discussion above) as tension is applied to the proximal end of the constraining fiber 7500, the intermediate portion 7508 of the constraining fiber 7500 laced about the medical device 7400 is operable to cause a constriction or reduction in the cross section of the portion of the medical device 7400 about which the intermediate portion 7508 is laced.

Likewise, as discussed above with respect to the medical device delivery system 6000, because the constraining fiber 7500 is removably coupled to the lockwire 7300, the constraining fiber 7500 can be decoupled from the lockwire 7300 after the medical device 7400 is properly oriented and deployed. Specifically, the lockwire 7300 may be withdrawn from the lockwire lumen of the olive 7200 such that the constraining fiber 7500 can be decoupled from the lockwire 7300. Thereafter, the lockwire 7300 and the constraining fiber 7500 may be removed from the body, though removal may not be required (as discussed above).

While the above-discussed example includes a medical device delivery system including an alignment mechanism situated between the proximal end of the constraining fiber 7500 and the medical device 7400, it should be appreciated that the constraining fiber 7500 may be situated between the distal end of the constraining fiber 7500 and the medical device 7400. In such examples, after being routed about the periphery of the medical device 7400 and before extending to the lockwire 7300, the constraining fiber 7500 is routed through the alignment mechanism 7700.

Figure 8:
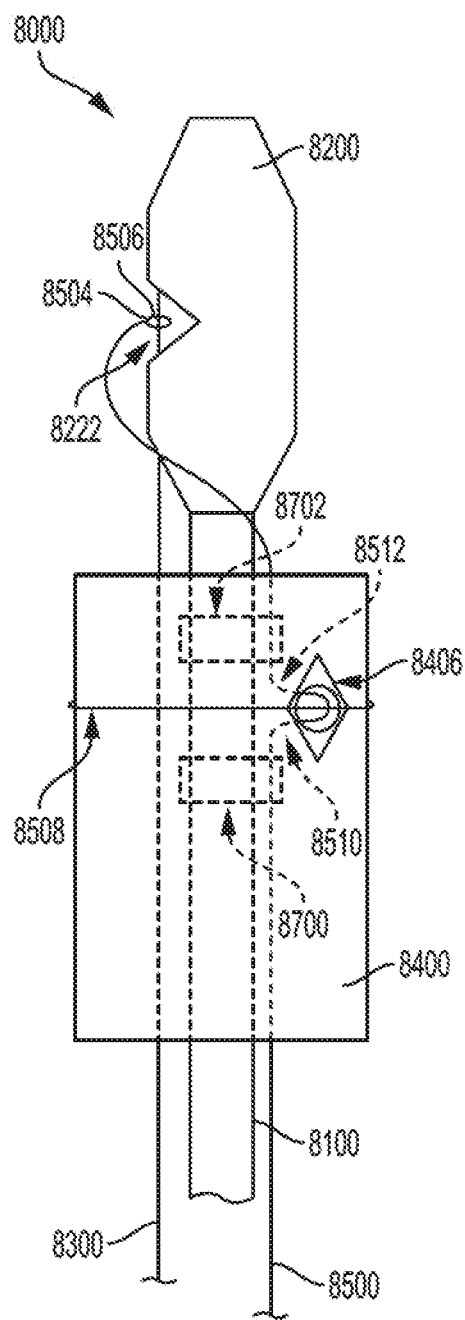
FIG. 8 is an illustration of a medical device delivery system consistent with various aspects of the present disclosure.

Additionally, while the above-discussed example includes a medical device delivery system including a single alignment mechanism, in some examples, a plurality of alignment mechanisms may be incorporated. Turning now to FIG. 8, a medical device delivery system 8000 is illustrated as including an elongate element 8100, an olive 8200, a lockwire 8300, and a constraining element, such as constraining fiber 8500. The elongate element 8100, the olive 8200, the lockwire 8300, and the constraining fiber 8500 are consistent with the various elongate elements, olives, lockwires, and constraining fibers discussed herein. It should be appreciated that while the examples below refer to the constraining element as a constraining fiber 8500, such reference should not be interpreted as limiting. For instance, it should be appreciated that the constraining element may be a structure that is suitable for being placed in tension, compression, or tension and compression.

In addition, the medical device delivery system 8000 includes a first alignment mechanism 8700 and a second alignment mechanism 8702. The alignment mechanism 8700 is similar to that alignment mechanism 7700 discussed above. The alignment mechanism 8702 is also similar to the alignment mechanism 7700 except that the constraining fiber 8500 is routed through the alignment mechanism 8702 after being routed about the periphery of the medical device 8400. Thus, the alignment mechanism 8702 is situated along the elongate element 8100 between the distal end 8504 and the portion of the constraining fiber 8500 that is routed about the medical device 8400.

As shown in FIG. 8, the constraining fiber 8500 is routed such that a portion of the constraining fiber 8500 extends from a proximal end (not illustrated in FIG. 8) to the first alignment mechanism 8700. The constraining fiber 8500 is routed through the first alignment mechanism 8700 and to the medical device 8400 such that a portion of the constraining fiber 8500 extends between the first alignment mechanism 8700 and the medical device 8400. As shown, the constraining fiber 8500 is routed through an aperture 8406 in the medical device 8400 and around a periphery of the medical device 8400. Thereafter, the constraining fiber 8500 is routed to the second alignment mechanism 8702. After being routed through the second alignment mechanism 8702, the constraining fiber 8500 extends to a position where the constraining fiber 8500 is coupled to the portion of the lockwire 8300 that is inserted in the lockwire lumen and exposed by the lockwire exposure feature 8222.

Like the constraining fiber 7500 illustrated in FIG. 7, the constraining fiber 8500 is routed about the periphery of the medical device 8400 such that, after extending about the periphery of the medical device 8400, the constraining fiber extends back through the aperture 8406 before extending to where it is coupled to the lockwire 8300. As shown, the portion of the constraining fiber 8500 that extends to the second alignment mechanism 8702 overlaps or otherwise loops around the portion of the constraining fiber 8500 extending from the alignment mechanism 8700.

In some examples, the first and second alignment mechanisms 8700 and 8702 are coupled to the elongate element 8100. In some such examples, the first and second alignment mechanisms 8700 and 8702 are positioned along a length of the elongate element 8100 such that, as tension is applied to the constraining fiber 8500, the longitudinal forces exerted on the medical device 8400 by the portions of the constraining fiber extending between the first and second alignment mechanisms 8700 and 8702 cancel each other out.

Specifically, as tension is applied to the constraining fiber 8500, a first force is exerted on the medical device 8400 by the portion of the constraining fiber 8500 extending between the first alignment mechanism 8700 and the medical device 8400 (i.e., constraining fiber portion 8510). This first force is directed along the constraining fiber portion 8510. Likewise, as the tension is applied to the constraining fiber 8500, a second force is exerted on the medical device 8400 by the portion of the constraining fiber 8500 extending between the second alignment mechanism 8702 and the medical device 8400 (i.e., constraining fiber portion 8512). This second force is directed along the constraining fiber portion 8512. As mentioned above, in some examples, the alignment mechanism 8700 and 8702 are positioned such that the first and second forces cancel each other out. Such a configuration provides that the portion of the medical device 8400 about which the constraining fiber 8500 is routed can be reduced in cross section while maintaining a position of the medical device 8400 along the medical device delivery system 8000.

In some other examples, the first and second alignment mechanisms 8700 and 8702 are positioned along a length of the elongate element 8100 such that, as tension is applied to the constraining fiber 8500, the longitudinal forces exerted on the medical device 8400 by the portions of the constraining fiber extending between the medical device 8400 and the first and second alignment mechanisms 8700 and 8702 are non-equal. In some such examples, the first alignment mechanism 8700 is situated along the elongate element 8100 such that it is a first longitudinal distance from the portion of the medical device 8400 about which the constraining fiber 8500 is routed while the second alignment mechanism 8702 is situated along the elongate element 8100 such that it is a second, different longitudinal distance from the portion of the medical device 8400 about which the constraining fiber 8500 is routed.

In these examples, the component forces exerted on the medical device 8400 by the constraining fiber portions 8510 and 8512 do not cancel each other out. Instead, as those of skill in the art will appreciate, the constraining fiber portion extending to the alignment mechanisms that is more longitudinally offset will be associated with the larger component of force. However, even in such examples, the distance by which the medical device 8400 is offset relative to the first and second alignment mechanisms 8700 and 8702 can be limited such that a resulting longitudinal component force is insufficient to cause displacement of the medical device 8400 along the longitudinal axis of the medical device delivery system 8000.

Accordingly, those of skill should appreciate that configurations incorporating such first and second alignment mechanisms can provide for medical device delivery systems that enable selective reduction of the cross sectional area of a medical device (e.g., for final positioning or reposition within the vasculature) without causing significant bias of the medical device along the longitudinal axis of the medical device delivery system While certain of the examples discussed above include the constraining fiber being coupled to a deployment sheath, in some other examples, the constraining fiber is additionally or alternatively coupled to the medical device. That is, in some examples, the constraining fiber directly couples the medical device to the lockwire. In some such examples, the medical device may comprise apices, knobs, eyelets, holes, or any other mechanisms suitable for attachment to the constraining fiber. Generally, in such examples, the proximal end of the constraining fiber is coupled to one of the above-referenced mechanisms suitable for attachment (e.g., apices, knobs, eyelets, holes, etc. of the medical device) while the distal end of the constraining fiber is coupled to the portion of the lockwire exposed by the lockwire exposure feature of the olive, as discussed herein. As similarly discussed above, it should appreciate that while the constraining fiber 3500 in this example is not directly coupled to the deployment sheath, the friction between the deployment sheath and the medical device operates to maintain a relative position between the medical device and the deployment sheath. Thus, if the constraining fiber operates to constrain the medical device against longitudinal translation along the elongate element, the constraining fiber likewise operates to constrain the deployment sheath against longitudinal translation along the elongate element.

As mentioned above, in some examples, the constraining fiber is directly coupled to both the deployment sheath and the medical device. In some such examples, a distal end of the constraining fiber is coupled to both the deployment sheath and the medical device. In some examples, the constraining fiber is routed through an attachment feature of the deployment sheath (e.g., a stitch, a hole, etc.) and coupled to the medical device. In some examples, the constraining fiber is routed through an attachment feature of the medical device (e.g., a stitch, an apex, a hole, etc.) and coupled to the deployment sheath.

Figure 9:
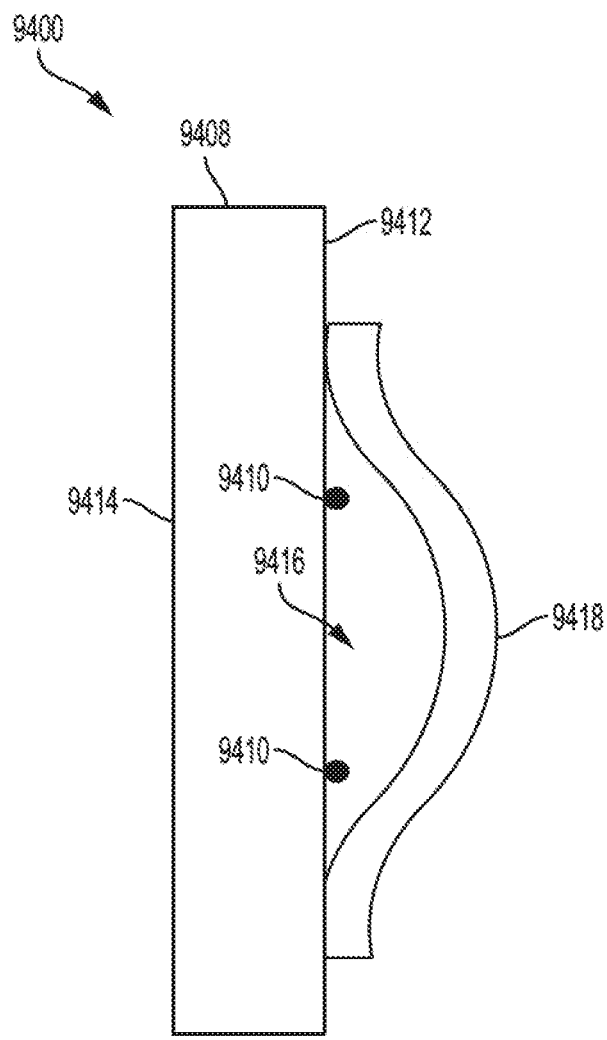
FIG. 9 is a cross-sectional view of a medical device and constraining line conduit in accordance with various aspects of the present disclosure.

Additionally, as discussed above, in some examples, the constraining fiber extends within an integrated constraining lumen. A cross sectional view of an exemplary integrated constraining lumen is illustrated in FIG. 9. As shown, in some examples, a medical device 9400 may include a graft portion 9408 and a stent portion 9410. The stent portion 9410 may be arranged on an exterior surface 9412 of the graft portion 9408. The graft portion 9408 also includes an interior surface 9414, which forms an internal lumen of the medical device 9400. The constraining element conduit 9416 (e.g., integrated constraining lumen) may be arranged around a circumference of the medical device 9400 on the exterior surface 9412 of the graft portion 9408 with the stent portion 9410 being arranged between the exterior surface 9412 of the graft portion 9408 and the constraining element conduit 9416. The constraining element conduit 9416 may include a discontinuity or gap at some point around the circumference of the medical device 9400. The discontinuity or gap in the constraining element conduit 9416 may allow for a constraining fiber (or line or wire) to be arranged through the constraining element conduit 9416.

The constraining element conduit 9416 may be formed by a graft portion 9418 that is attached to the exterior surface 9412 of the graft portion 9408. In addition, the constraining element conduit 9416 may include a first boundary and a second boundary. As shown in FIG. 9, the first boundary of the constraining element conduit 9416 is the exterior surface 9412 of the graft portion 9408, and the second boundary is formed by the graft portion 9418. As a result, the constraining element conduit 9416 may provide a pathway through which a constraining fiber (or line or wire) (not shown) may be arranged. The constraining fiber (or line or wire) may constrain the medical device 9400 axially and/or radially in response to tension applied thereto.

Figure 10C:
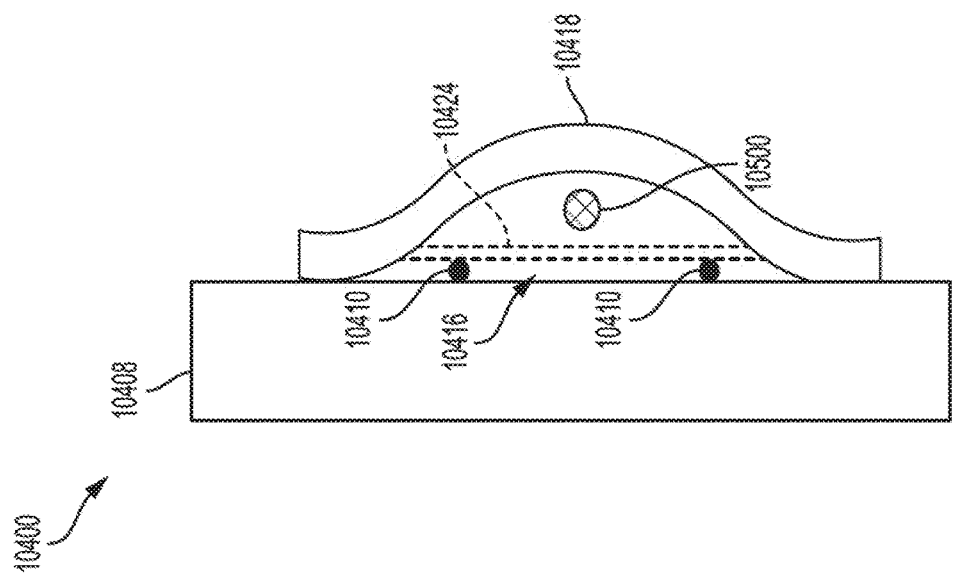
FIG. 10C is a cross-sectional view of a medical device and constraining line conduit with an optional additional graft layer in accordance with various aspects of the present disclosure.
Figure 10B:
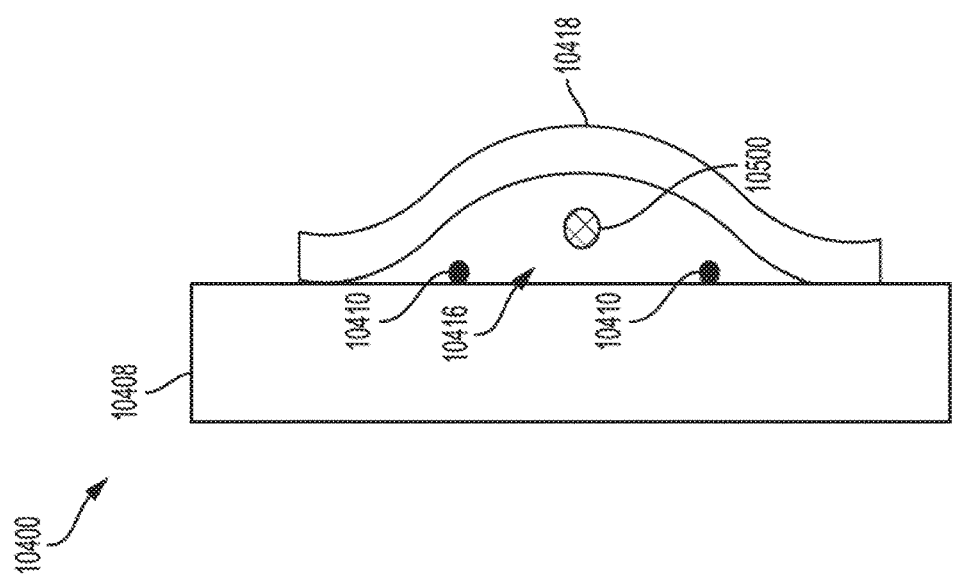
FIG. 10B is a cross-sectional view of the medical device and constraining line conduit, as shown in FIG. 10A, with a constraining fiber arranged through the constraining line conduit in accordance with various aspects of the present disclosure.
Figure 10A:
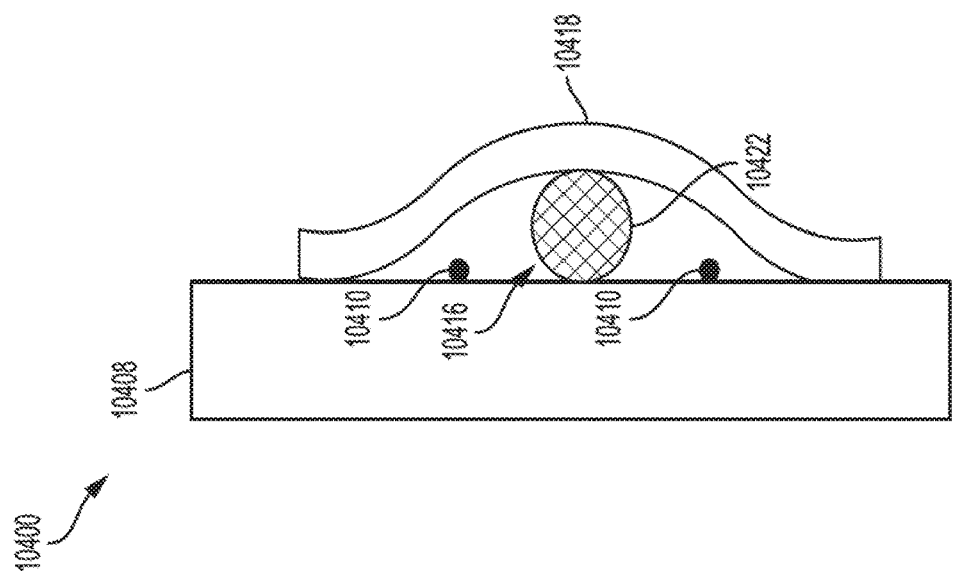
FIG. 10A is a cross-sectional view of a medical device and constraining line conduit with a wire that may be used to form a constraining line conduit in accordance with various aspects of the present disclosure.

FIG. 10A is a cross-sectional view of the medical device 10400 and constraining element conduit 10416. The medical device 10400 may include a graft portion 10408 and a stent portion 10410. The stent portion 10410 may be arranged on an exterior surface of the graft portion 10408. The constraining element conduit 10416 may be formed by a first graft portion 10418 that is attached to the exterior surface of the graft portion 10408. The first graft portion 10418 may be bonded on the exterior surface of the graft portion 10408. As shown in FIG. 10A, a wire (or alternatively a fiber) 10422 may be arranged between the exterior surface of the graft portion 10408 and the first graft portion 10418. The wire 10422 may provide an obstruction during bonding of the first graft portion 10418 to the exterior surface of the graft portion 10408 such that end portions of the first graft portion 10418 is bonded to the exterior surface of the graft portion 10408.

After the first graft portion 10418 is bonded to the exterior surface of the graft portion 10408, the wire 10422 may be removed. FIG. 10B is a cross-sectional view of the medical device 10400 and the constraining element conduit 10416, as shown in FIG. 10A, that results from the wire 10422 providing an obstruction to bond the end portions of the first graft portion 10418 is bonded to the exterior surface of the graft portion 10408. As shown in FIG. 10B, the wire 10422 leaves behind a passage of the constraining element conduit 10416 through which a constraining fiber 10500 may be arranged. As a result, the constraining element conduit 10416 may include a first boundary and a second boundary. As shown in FIG. 10B, the first boundary of the constraining element conduit 10416 is the exterior surface of the graft portion 10408, and the second boundary is formed by the first graft portion 10418.

In certain instances, a second graft portion 10424 may be arranged over the stent 10410 within the bounds of the first graft portion 10418. The second graft portion 10424 may be bonded to the exterior surface of the graft portion similar to manner in which the first graft portion 10418 is bonded to the exterior surface of the graft portion 10408 (e.g., an FEP adhesive). FIG. 10C is a cross-sectional view of the medical device 10400, the constraining fiber conduit 10416, and the constraining fiber 10500, as shown in FIGS. 10A-B, with second (additional) graft portion 10424 in accordance with various aspects of the present disclosure. As a result, the second graft portion 10424 may form the first boundary of the constraining fiber conduit 10416, with the first graft portion 10418 forming the second boundary. The constraining fiber conduit 10416 may include a discontinuity or gap at some point around the circumference of the medical device 10400. The discontinuity or gap in the constraining fiber conduit 10416 may allow for the constraining fiber 10500 to be arranged through the constraining fiber conduit 10416. More specifically, the circumference of the medical device 10400 may be between 25 mm and 50 mm. The discontinuity or gap in the constraining fiber conduit 10416 may be between 0.5 mm and 3 mm. The remaining portions of the constraining fiber conduit 10416 are continuous about the circumference of the medical device 10400.

The constraining fiber 10500 may constrain the medical device 10400 axially and/or radially in response to tension applied thereto. In addition, the medical device 10400 may be constrained and unconstrained using the constraining fiber 10500 between a constrained configuration (e.g., for delivery of the medical device 10400) and a deployed configuration (e.g., an operative state at a target therapy region). The implantable device 10400 may be constrained and unconstrained multiple times to allow for repositioning of the implantable device 10400 at the therapy location if the positioning is not desirable.

Though not explicitly illustrated or referred to in each of the above-discussed examples, those of skill should appreciate that the various medical device delivery systems described herein are deliverable though a delivery catheter (see for example the delivery catheter configuration illustrated and described in FIGS. 5A and 5B). Likewise, though not explicitly illustrated or referred to in each of the above-discussed examples, those of skill should appreciate that the various medical device delivery systems may include a control system coupled at a proximal end thereof, such as outside the patient's body or vasculature.

While the examples described and illustrated above include an elongate element having an olive coupled thereto, in some other examples, the elongate element may alternatively comprise a blunt, rounded, or tapered distal tip. That is, instead of coupling an olive to the elongate element, the distal end of the elongate element, itself, includes an integrally formed blunt, rounded, or tapered distal tip. In some examples, the distal tip of the elongate element can be characterized by varying degrees of rigidity or softness, which can further vary along the length of the elongate element.

Likewise, while the olive 1200 is illustrated and described as being generally cylindrical, it should be appreciated that the olive 1200 can be of any suitable size and can have any shape suitable for navigating the vasculature without departing from the spirit or scope of the present disclosure.

The inventive scope of this application has been described above both generically and with regard to various embodiments by way of example. It will be apparent to those skilled in the art that various modifications and variations can be made in to the embodiments, including combination of features from the various embodiments, without departing from the scope of invention. It is intended that the scope of invention include such modifications and variations.

What is claimed is:
1. A medical device delivery system comprising:
an elongate element;
an olive coupled to the elongate element, the olive including a body having a proximal end, a distal end, and an outer surface, the olive including a lockwire lumen and the body having a lockwire exposure feature formed in the outer surface of the body between the proximal and distal ends such that a portion of the lockwire lumen is exposed;
a lockwire removably coupled to the olive, the lockwire extending through the lockwire lumen such that a longitudinally-extending portion of the lockwire is exposed by the lockwire exposure feature formed in the outer surface of the body of the olive, and
a linking element removably coupled to the portion of the lockwire extending through the lockwire lumen and exposed by the lockwire exposure feature formed in the body of the olive.
2. The system of claim 1, wherein the linking element has a first end and a second end, the first end of the linking element being removably coupled to the longitudinally-extending portion of the lockwire extending through the lockwire lumen and exposed by the lockwire exposure feature formed in the body of the olive such that the first end of the linking element is constrained against longitudinal translation along the lockwire beyond the proximal and distal ends of the olive.
3. The system of claim 2, wherein the linking element operates to maintain a position of a medical device along the elongate element during a delivery and deployment of the medical device to a target region within a patient's vasculature.
4. The system of claim 3, wherein the second end of the linking element is configured to be coupled to the medical device.
5. The system of claim 3, wherein the second end of the linking element is coupled to the olive such that an intermediate portion of the linking element is configured to be routed through an aperture in the medical device.
6. The system of claim 3, wherein the linking element includes an intermediate portion situated between the first and second ends of the linking element, the intermediate portion configured to be coupled to the medical device and being operable to reduce a cross section of the medical device when tension is applied to the second end of the linking element.
7. The system of claim 6, wherein the intermediate portion of the linking element is configured to be routed about a periphery of the medical device.
8. The system of claim 3, wherein the linking element is configured to be removable from the medical device.
9. The system of claim 1, further comprising a first alignment mechanism coupled to the elongate element, the linking element being routed through the first alignment mechanism.
10. The system of claim 9, wherein the first alignment mechanism is positioned along the elongate element such that a portion of the linking element proximal the intermediate portion is routed through the first alignment mechanism.
11. The system of claim 9, further comprising a second alignment mechanism coupled to the elongate element, the second alignment mechanism being positioned along the elongate element such that a portion of the linking element distal the intermediate portion is routed through the second alignment mechanism.

12. The system of claim 11, wherein the first and second alignment mechanisms are positioned along the elongate element such that, as tension is applied to the linking element, a first longitudinally directed force exerted on medical device by the portion of the linking element extending between the first alignment mechanism and the medical device is counteracted by a second longitudinally directed force exerted on medical device by the portion of the linking element extending between the second alignment mechanism and the medical device.

13. The system of claim 3, wherein a tension can be applied to the linking element to reduce a cross section of the medical device without causing translation of the medical device.

14. The system of claim 9, wherein the first alignment mechanism is positioned along the elongate element such that a portion of the linking element distal the intermediate portion is routed through the first alignment mechanism.

15. The system of claim 1, wherein the linking element is a steering element and is operable to deflect the olive when tension is applied to the second end of the linking element.

16. The system of claim 1, wherein the lockwire exposure feature formed in the body between the proximal and distal ends bisects the lockwire lumen such that the lockwire lumen includes a proximal portion and a distal portion.

17. The system of claim 16, wherein the proximal and distal portions of the lockwire lumen are separated by a gap, and wherein the lockwire extends across the gap such that the lockwire is received within the proximal and distal portions of the lockwire lumen.

18. The system of claim 1, wherein the olive further comprises a guidewire lumen, the lockwire lumen being laterally offset from the guidewire lumen.

19. The system of claim 1, wherein the linking element is compressible.

20. A method of releasably coupling a constraining element to an olive, the method comprising:
  providing an olive coupled to a distal end of an elongate element, the olive including a body having a proximal end and a distal end, the olive including a lumen and the body of the olive having an opening formed therein, the opening being formed in the body of the olive between the proximal and distal ends such that a portion of the lumen is exposed and such that the opening bisects the lumen such that lumen comprises a proximal portion and a distal portion;
  routing a linking element to the olive such that a portion of the linking element is positioned within the lumen of the olive;
  positioning a distal end of the linking element in the opening formed in the olive such that the distal end of the linking element is situated between the proximal and distal portions of the lumen;
  inserting a lockwire into the proximal portion of the lumen; and
  advancing the lockwire through the proximal portion of the lumen and into the distal portion of the lumen such that the lockwire engages the linking element and constrains a distal end of the linking element from longitudinal translation along the lockwire beyond the proximal and distal ends of the olive.

21. The method of claim 20, wherein withdrawing the lockwire from the distal portion of the lumen such that a distal end of the lockwire is positioned within the proximal portion of the lumen operates to decouple the linking element from the lockwire.

22. A medical device delivery system comprising:
  an elongate element;
  an olive coupled to the elongate element, the olive including a body having a proximal end, a distal end, the olive including a lockwire lumen and the body having an opening formed therein, the opening being formed in the body between the proximal and distal ends such that a portion of the lockwire lumen is exposed;
  a lockwire removably coupled to the olive, the lockwire extending through the lockwire lumen such that a portion of the lockwire is exposed by the opening formed in the body of the olive;
  a linking element removably coupled to the portion of the lockwire extending through the lockwire lumen and exposed by the opening formed in the body of the olive; and
  a first alignment mechanism coupled to the elongate element, the linking element being routed through the first alignment mechanism.

23. The system of claim 22, wherein the first alignment mechanism is positioned along the elongate element such that a portion of the linking element proximal the intermediate portion is routed through the first alignment mechanism.

24. The system of claim 22, further comprising a second alignment mechanism coupled to the elongate element, the second alignment mechanism being positioned along the elongate element such that a portion of the linking element distal the intermediate portion is routed through the second alignment mechanism.

25. The system of claim 24, wherein the first and second alignment mechanisms are positioned along the elongate element such that, as tension is applied to the linking element, a first longitudinally directed force exerted on medical device by the portion of the linking element extending between the first alignment mechanism and the medical device is counteracted by a second longitudinally directed force exerted on medical device by the portion of the linking element extending between the second alignment mechanism and the medical device.

26. The system of claim 22, wherein the first alignment mechanism is positioned along the elongate element such that a portion of the linking element distal the intermediate portion is routed through the first alignment mechanism.

27. A medical device delivery system comprising:
  an elongate element;
  an olive coupled to the elongate element, the olive including a body having a proximal end, a distal end, the olive including a lockwire lumen and the body having an opening formed therein, the opening being formed in the body between the proximal and distal ends to bisect the lockwire lumen such that the lockwire lumen includes a proximal portion and a distal portion and such that a portion of the lockwire lumen is exposed;
  a lockwire removably coupled to the olive, the lockwire extending through the lockwire lumen such that a portion of the lockwire is exposed by the opening formed in the body of the olive; and
  a linking element removably coupled to the portion of the lockwire extending through the lockwire lumen and exposed by the opening formed in the body of the olive.

28. The system of claim 27, wherein the proximal and distal portions of the lockwire lumen are separated by a gap, and wherein the lockwire extends across the gap such that the lockwire is received within the proximal and distal portions of the lockwire lumen.

\* \* \* \* \*